(12) United States Patent
ÓLaighin et al.

(10) Patent No.: US 10,744,324 B2
(45) Date of Patent: Aug. 18, 2020

(54) APPARATUS FOR MANAGEMENT OF A PARKINSON'S DISEASE PATIENT'S GAIT

(71) Applicant: NATIONAL UNIVERSITY OF IRELAND, GALWAY, Galway (IE)

(72) Inventors: Gearóid Ó Laighin, Salthill (IE); Leo Quinlan, Oranmore (IE); Dean Sweeney, Stranorlar (IE); Gavin Corley, Ennis (IE); James Feehilly, Tuam (IE); Patrick Browne, Ballinasloe (IE)

(73) Assignee: National University of Ireland, Galway, Galway (IE)

( * ) Notice: Subject to any disclaimer, the term of this patent is extended or adjusted under 35 U.S.C. 154(b) by 140 days.

(21) Appl. No.: 15/566,967

(22) PCT Filed: Apr. 15, 2016

(86) PCT No.: PCT/EP2016/058341
§ 371 (c)(1),
(2) Date: Oct. 16, 2017

(87) PCT Pub. No.: WO2016/166281
PCT Pub. Date: Oct. 20, 2016

(65) Prior Publication Data
US 2018/0140842 A1 May 24, 2018

(30) Foreign Application Priority Data

Apr. 17, 2015 (EP) .................................. 15163987

(51) Int. Cl.
*A61N 1/36* (2006.01)
*A61H 3/00* (2006.01)

(52) U.S. Cl.
CPC ........... *A61N 1/36067* (2013.01); *A61H 3/00* (2013.01); *A61N 1/36003* (2013.01);
(Continued)

(58) Field of Classification Search
CPC ............ A61N 1/36067; A61N 1/36003; A61H 2003/007; A61H 2201/165;
(Continued)

(56) References Cited

U.S. PATENT DOCUMENTS

| 7,917,225 B2 | 3/2011 | Wyler et al. |
| 2007/0250134 A1 * | 10/2007 | Miesel ................. A61B 5/0488 607/45 |

(Continued)

FOREIGN PATENT DOCUMENTS

| EP | 1 558 333 A1 | 8/2005 |
| EP | 2 586 489 B1 | 12/2014 |
| WO | 2004/037344 A1 | 5/2004 |

OTHER PUBLICATIONS

International Preliminary Report on Patentability issued in PCT/EP2016/058341; dated Oct. 17, 2017; 8pp.
(Continued)

*Primary Examiner* — Paula J Stice
(74) *Attorney, Agent, or Firm* — Studebaker & Brackett PC

(57) ABSTRACT

A gait management apparatus applies stimulation to a user suffering from a neurological disease (such as Parkinson's Disease) gait dysfunction. Motion sensors are arranged to be worn by a patient, and electrical stimulation electrodes are on the legs for stimulation. A controller receives motion sensing signals, and processes these signals to generate stimulation signals for operation of the electrodes to stimulate limb movement upon detection of a gait abnormality. There may be a user actuator for user actuation of electrical stimulation, and the inputs may be a series of taps. The controller may provide signals to prevent occurrence of freezing of gait when it senses that a patient is walking or has an intention to walk. Also, it may apply stimulation at an
(Continued)

intensity level which is insufficient for functional muscle stimulation but sufficiently high to trigger activation of efferent nerves.

37 Claims, 16 Drawing Sheets

(52) U.S. Cl.
CPC .. *A61H 2003/007* (2013.01); *A61H 2201/165* (2013.01); *A61H 2201/5023* (2013.01); *A61H 2201/5079* (2013.01); *A61H 2201/5084* (2013.01); *A61H 2230/105* (2013.01)

(58) Field of Classification Search
CPC .... A61H 2201/5023; A61H 2201/5079; A61H 2201/5082; A61H 2230/105
See application file for complete search history.

(56) References Cited

U.S. PATENT DOCUMENTS

| | | |
|---|---|---|
| 2009/0099627 A1 | 4/2009 | Molnar et al. |
| 2014/0249452 A1 | 9/2014 | Marsh et al. |
| 2014/0249600 A1 | 9/2014 | Heruth et al. |

OTHER PUBLICATIONS

International Search Report issued in PCT/EP2016/058341; dated Jun. 15, 2016.

\* cited by examiner

Time of complete Task   Average Walking speed

% of time in FOG

Cutaneous Somatosensory Stimulation

Motor Somatosensory Stimulation

APPARATUS FOR MANAGEMENT OF A PARKINSON'S DISEASE PATIENT'S GAIT

INTRODUCTION

Field of the Invention

The invention relates to the management of gait for persons suffering from Parkinson's disease or with similar neurological conditions.

Prior Art Discussion

Parkinson's disease ("PD") is a progressive neurological condition resulting from the loss of dopaminergic neurons in a specialized area of the brain called the substantia nigra. PD can present at any age, however less than 10% of cases are reported before the age of 40. The annual incidence of PD in Europe is 10-20 cases/100,000 inhabitants/year. Approximately 1.6% of people aged over 65 years have PD. There are approximately 5.2 million PD patients worldwide and they have a mortality that is 2 to 5 times higher than age-matched controls. The majority of PD patients are elderly people and this population cohort is expanding rapidly. Thus PD is becoming an increasing public health and socioeconomic challenge. The primary issues in PD are due to reduced capacity for self-care, performance of activities of daily living and reduced quality of life. The high healthcare costs involved with PD (medical and social) are considerable and affect multiple sectors. The main elements of this cost base are hospital care and prescription drugs. PD patients have 45% more hospitalizations and typically stay 20% longer in hospital than disease free age-matched populations.

Gait disturbances are a common feature of neurological disease. Particularly in people with Parkinson's disease, gait disturbances have a significant impact on daily life and often lead to falls and hospitalisation.

The symptoms of PD can be broadly classified into motor symptoms and non-motor symptoms.

Motor symptoms (MS) include rigidity, tremor, bradykinesia (slow movement) and postural alterations. These symptoms are cardinal features of PD and contribute to progressive gait disturbances, which are strongly linked to a reduced quality of life. These gait disturbances present in terms of a reduction in stride length and walking speed, increased stride variability and episodes called Freezing Of Gait (FOG). Gait alterations in PD become increasingly problematic as the disease advances despite best pharmacological therapy. In particular, FOG occurs in excess of 40% of PD patients and is characterized by a rapid onset and variable duration (typically <1 min) causing a breakdown in gait fluency. FOG can appear in the initiation of gait or randomly within the gait cycle and is often medication refractory leading to it being a major source of disability for PD patients. FOG can affect people both in the so-called "ON" state (i.e. on normal prescribed medications and the medication effects of the medications are still present) and in the so called "OFF" state (i.e. where the effect of normal medication has worn off).

The biological mechanisms underlying FOG are yet to be elucidated. The most common forms of FOG are reported to be initiation FOG or turning FOG. Attempting to walk in narrow passageways, adjusting one's stride length when reaching a destination, and stressful situations also commonly trigger FOG. The gait disturbances associated with PD and in particular FOG can lead to falls. In PD populations falls are a leading cause of morbidity and mortality.

The primary treatment for PD symptoms is to prescribe drugs such as Levodopa™, a precursor for the neurotransmitter dopamine. This replacement therapy aims to replace endogenous dopamine that is lost due to neurodegeneration in the brain. Commonly, symptoms such as FOG can be medication refractory. Thus conventional therapy for gait disturbance is based on clinical diagnosis of a disturbance and appropriate alteration of the profile and dosage of medication. However a significant issue for PD patients is that the effectiveness of the drugs diminishes over time, leading to the condition as a whole becoming resistant to current pharmacological therapies.

Other therapies do exist, for example Deep Brain Stimulation (DBS), but not all patients are suitable for this type of intervention and the therapy is highly invasive and highly expensive. DBS is a neurosurgical procedure, which involves the implantation of a medical device, sometimes called a brain pacemaker, which sends electrical impulses, through implanted electrodes to specific parts of the brain for the treatment of movement and affective disorders. A deep brain stimulator requires the implantation of all components of the apparatus. The lead with electrodes is placed in the brain and the implanted pulse generator (IPG) is implanted subcutaneously below the clavicle or in the abdomen, with an insulated wire running from the IPG to the lead in the brain. The wire is routed below the skin, from the head, down the side of the neck, behind the ear to the IPG. Lead implantation involves an approximately 14 mm hole being drilled in the skull.

There is mounting evidence from a range of studies that cueing methodologies can improve gait performance in PD populations. These cues are temporal, spatial, audio or visual stimuli, which facilitate the initiation and continuation of repetitive sequential movements such as gait and can assist in handling, or even overcoming, gait irregularities, in particular freezing of gait episodes.

Some devices have been developed that provide cues as a means to stop gait irregularities. Other devices have been developed that provide cues as a means to prevent gait irregularities occurring in the first place. Such devices are activated (manually or automatically) when motion is detected, and provide continuous cueing, by for example repetitive sound from a metronome being delivered via an earpiece. More advanced systems aim to assess user cadence and adapt the delivered cue rhythm to the user's normal gait. An example of such a system is described in US201214124752.

The cue is normally intended to provide supportive information to the PD patient about step frequency or amplitude leading to a change in the motor response of the subject. The mechanism by which established cueing modalities work is not proven but reports suggest activation of alternate neural pathways bypassing the defective basal ganglia and accessing the motor programs controlling gait.

It appears that the technologies used to implement the prior systems are not very compatible with normal daily living requirements. They have the disadvantage of not being very discreet (earpiece worn on the ear, light-wand carried by patient) and they can be ineffective in busy, bright (seeing the light pattern from the light-wand/distinguishing the light pattern from the light-wand from varying ambient light conditions) or noisy (hearing the audio cue in your earpiece while being subject to a range of ambient noises) environments that one can typically encounter as you go about your daily life.

U.S. Pat. No. 7,917,225 (Advanced Neuromodulation Systems) describes application of electrical stimulation to a location of a patient's brain in response to a range of disorders including movement disorder. The approach proposed involves an invasive surgery to implant one or more electrodes directly at identified brain sites in the central nervous system.

EP2586489 (Bioness Neuromodulation Ltd) describes a system for improved stimulation systems based on gait signals associated with heel-contact events. It discloses improvements for force-sensitive resistors as part of an FES device system for controlling lower limb muscle contractions. The disclosure includes stimulation of muscles of the lower limb to control and guide muscle activity related to gait characteristics determined by a foot pressure sensor.

US2009/0099627 (Molnar et al) discloses detection of a movement state based on brain signals such as an electroencephalogram (ECG) signals, and delivery of a movement disorder therapy in the form a cue elicited by mechanical vibration applied to the skin. The therapy cue may be functional electrical stimulation (FES) or transcutaneous electrical stimulation (TENS) of a muscle or muscle group in order to help initiate movement or help a patient to control movement of a limb or other body part.

US2014/0249600 (Heruth et al) discloses detection of a patient's gait parameter, and providing stimulation by way of electrodes in the brain.

US2014/0249452 (March et al) discloses a freezing of gait cue apparatus. A visual cue is provided, in the form of a light beam on the ground.

The invention is directed towards providing a simpler and/or more effective system for improved management of gait problems in patients.

SUMMARY OF THE INVENTION

According to the invention, there is provided a gait management apparatus comprising:
- at least one motion sensor,
- at least one cueing actuator with electrical stimulation electrodes,
- a controller configured to process motion sensing signals from said at least one motion sensor, to perform automatic detection of a gait dysfunction or potential gait dysfunction, and to activate said cueing actuator automatically upon said detection,
- wherein the controller and the cueing actuator are configured to perform sensory level cueing and motor level cueing,
- wherein the controller is configured to determine if cueing at a sensory level is required or if cueing at a motor level is required, and to provide output signals to the cueing actuator accordingly, and
- wherein the controller is configured to determine characteristics of a patient and to activate cueing customised to the patient.

In one embodiment, said gait dysfunction is freezing of gait. In one embodiment, said characteristics include skin impendence, and/or sensory threshold, and/or motor threshold, and/or pain threshold, and/or pain tolerance. In one embodiment, said characteristics include the patient's changing response to motor level stimulation as a cue and/or the patient's changing response to sensory level stimulation as a cue.

In one embodiment, the controller is configured to activate the cueing actuator to prevent gait dysfunction when the controller senses that a patient is walking or has an intention to walk.

In one embodiment, the controller is configured to apply electrical stimulation cueing at an intensity level which is insufficient for functional muscle contraction, in which said cueing includes stimulation of either afferent or efferent nerves, in which afferent nerve stimulation causes a patient central nervous system to cause an action, and efferent nerve stimulation directly causes a muscle contraction with consequent triggering of afferent nerves causing the patient's central nervous system to trigger an action giving rise to a natural motor response, and in which said efferent nerve cueing is at an intensity level which is insufficient for functional muscle contraction.

In one embodiment, the controller is configured to control cueing to exceed a multi-modal somatosensory threshold but not to cause a functional muscular contraction, in which electrode stimulation intensity is across a full continuum from a simple muscle twitch response up to but not including a muscle contraction of sufficient intensity as would aid in the execution of a functional movement.

Preferably, the controller is configured to operate in a continuous cueing mode or an adaptive cueing mode, in which:
- in the continuous mode, cueing is performed whenever the user is not seated, standing still or lying, in which cueing is performed upon detection of intention to walk until the controller determines that the user stops walking, and
- in the adaptive mode cueing is performed to prevent freezing-of-gait only in response to alterations in gait dynamics or detection of a freezing-of-gait pre-cursor.

In one embodiment, the controller is configured to activate cueing with a series of bursts until it automatically determines that gait dysfunction has ended. In one embodiment, the controller is configured to dynamically modify cueing in real time according to conditions. Preferably, the controller is configured to modulate stimuli in real-time using closed loop control. In one embodiment, the controller is configured to maintain and monitor at least one three dimensional stimulus space, one for cutaneous multi-modal somatosensory electrical stimulation and/or one for motor multi-modal somatosensory electrical stimulation.

In one embodiment, the controller is configured to manage a stimulus effect of independent stimulation parameters working together to increase or decrease the effect of the electrical stimulus. In one embodiment, said parameters include stimulus intensity voltage, ramp-up time, and pulse Frequency. In one embodiment, the controller is configured to identify stimulus effect points in multi-dimensional space including lowest stimulus values considered to work for multi-modal somatosensory electrical stimulation and highest stimulus values that will maintain the stimulus as non-motor and still function as multi-modal somatosensory electrical stimulation.

In one embodiment, the controller is configured to modulate stimulus intensity by moving along a stimulation modulation profile line from a point of lowest intensity to a point of highest intensity with adjustment of all parameters simultaneously, using an adjustable window size. In one embodiment, the controller is configured to divide the stimulation modulation profile line into multiple steps from a minimum stimulus point to a maximum stimulus point.

In one embodiment, the controller is configured to operate in a freezing-of-gait prevention mode in which the controller measures a percentage of time the patient was in a freezing-of-gait state for a last time window and modulates stimulus to be used for a next cycle on the basis of this measurement. Preferably, the controller is configured to operate in the freezing-of-gait prevention mode at a lowest stimulation point while the patient is detected to be walking.

In one embodiment, the controller is configured to move along the line according to the extent of freezing-of-gait detected in a previous time window. In one embodiment, the controller is configured to choose per-patient a line to follow as part of the patient characteristics.

In one embodiment, the controller is configured to operate in a freezing-of-gait relief mode in which there is progressively greater stimuli applied in steps along said profile line until freezing-of-gait has stopped. In one embodiment, the controller is configured to receive a user input of how aggressively stimulus will be increased to relieve freezing-of-gait if it persists.

In one embodiment, the controller is configured to activate cueing by providing cueing signals with a pulse width of up to 1000 μs, and an inter-pulse interval of up to 1000 μs.

In one embodiment, the inter-pulse width is up to 100 μs. In one embodiment, the controller is configured to activate cueing by providing cueing signals with a pulse frequency of up to 60 Hz. In one embodiment, the controller is configured to activate cueing by providing cueing signals for a maximum electrode stimulation surface voltage of up to 100V. In one embodiment, the controller is configured to activate cueing by providing cueing signals for a maximum electrode stimulation surface voltage of up to 68V.

In one embodiment, at least some electrodes are implantable and the controller is configured to provide stimulation signals for said implantable electrodes to provide a current in the range up to 200 mA. In one embodiment, the controller is configured to provide stimulation signals for said implantable electrodes to provide a current in the range from 10 μA to 50 mA.

In one embodiment, the controller is configured to provide cueing actuator signals with an envelope having a ramp-up time of up to 5000 ms, an ON time of up to 10,000 ms, a ramp-down of up to 1000 ms, and an OFF time of up to 10,000 ms. In one embodiment, the ramp-down time is in the range of up to 500 ms and the OFF time is up to 5000 ms.

In one embodiment, at least one actuator pair of electrodes is arranged to be skin surface mounted. In one embodiment, at least one actuator pair of electrodes is arranged to be implanted under a patient's skin.

In one embodiment, the apparatus further comprises a patient interface, and the controller is configured to activate cueing in response to a manual cueing instruction at said interface. In one embodiment, the interface comprises a button for manual cueing activation.

In one embodiment, the controller is configured to recognise at least one tap as a patient trigger to activate cueing. In one embodiment, the controller is configured to be customised to parameters specific to a patient for recognising taps. Preferably, the controller is configured to recognise a series of multiple taps as said patient trigger. In one embodiment, the controller is configured to recognise a series of two taps as said patient trigger.

In one embodiment, the controller is configured to recognise said taps if they comply with parameters of (a) latency, being a minimum time which must elapse between the first and the second tap being performed, (b) threshold, which is a minimum acceleration which must be detected before an acceleration spike is recognised as a tap, (c) time limit, which is the maximum time which can elapse from the acceleration signal exceeding the threshold to returning below the threshold, and (d) window, which is the time after the latency, by which time the subsequent tap must have crossed the threshold.

In one embodiment, the controller is configured to operate with the following limits for said parameters: latency time up to 635 ms, threshold acceleration 5 m/s$^2$ to 100 m/s$^2$, time limit up to 1270 ms, and window time up to 1270 ms.

In one embodiment, the controller is configured to recognise said tapping on an enclosure of the controller.

In one embodiment, the apparatus comprises at least one accelerometer linked with the controller and the controller is configured to use inputs from said accelerometer as tap inputs.

In one embodiment, at least one cueing actuator is wirelessly linked with the controller, and the controller may include a smartphone programmed with apparatus control software.

In one embodiment, at least one cueing actuator is configured to be worn, for example wrist-worn.

In one embodiment, the cueing actuator includes a mechanical stimulation device.

In one embodiment, the mechanical stimulation device is configured to perform mechanical vibration.

In another aspect, the invention provides a gait management method comprising steps performed by a controller with a digital processor linked to at least one motion sensor and with at least one cueing actuator including electrical stimulation electrodes, the method including the steps of:

receiving patient motion signals from the at least one motion sensor, processing said motion sensing signals to perform automatic detection of a gait dysfunction or potential gait dysfunction, and activating the cueing actuator automatically upon said detection, in a manner customised to a patient and being at a sensory level or a motor level, according to said motion signals and characteristics of a patient.

In one embodiment, said gait dysfunction is freezing of gait.

In one embodiment, said characteristics include skin impendence, and/or sensory threshold, and/or motor threshold, and/or pain threshold, and/or pain tolerance.

In one embodiment, said characteristics include a patient's changing response to motor level stimulation as a cue and/or the patient's changing response to sensory level stimulation as a cue.

In one embodiment, the controller activates the cueing actuator to prevent gait dysfunction when the controller senses that a patient is walking or has an intention to walk.

In one embodiment, the controller applies electrical stimulation cueing at an intensity level which is insufficient for functional muscle contraction, in which said cueing includes stimulation of either afferent or efferent nerves, in which afferent nerve stimulation causes a patient central nervous system to cause an action, and efferent nerve stimulation directly causes a muscle contraction with consequent triggering of afferent nerves causing the patient's central nervous system to trigger an action giving rise to a natural motor response, and in which said efferent nerve cueing is at an intensity level which is insufficient for functional muscle contraction.

In one embodiment, the controller controls cueing to exceed a multi-modal somatosensory threshold but not to cause a functional muscular contraction, in which electrode stimulation intensity is across a full continuum from a twitch response up to but not including a muscle contraction of sufficient intensity as would aid in the execution of a functional movement.

In one embodiment, the controller operates in a continuous cueing mode or an adaptive cueing mode, in which:
  in the continuous mode, cueing is performed whenever the user is not seated, standing still or lying, in which cueing is performed upon detection of intention to walk until the controller determines that the user stops walking, and
  in the adaptive mode cueing is performed to prevent freezing-of-gait only in response to alterations in gait dynamics or detection of a freezing-of-gait pre-cursor.

In one embodiment, the controller activates cueing with a series of bursts until it automatically determines that gait dysfunction has ended. In one embodiment, the controller dynamically modifies cueing in real time according to conditions. In one embodiment, the controller modulates stimuli in real-time using closed loop control.

In one embodiment, the controller maintains and monitors at least one multi-dimensional stimulus space, one for cutaneous multi-modal somatosensory electrical stimulation and/or one for motor multi-modal somatosensory electrical stimulation.

In one embodiment, the controller manages a stimulus effect of independent stimulation parameters working together to increase or decrease the effect of the electrical stimulus.

In one embodiment, said parameters include stimulus intensity voltage, ramp-up time, and pulse frequency. In one embodiment, the controller identifies stimulus effect points in multi-dimensional space including lowest stimulus values considered to work for multi-modal somatosensory electrical stimulation and highest stimulus values that will maintain the stimulus as non-motor and still function as multi-modal somatosensory electrical stimulation, and the controller modulates stimulus intensity by moving along a stimulation modulation profile line from a point of lowest intensity to a point of highest intensity with adjustment of all parameters simultaneously, using an adjustable window size.

In one embodiment, the controller recognises at least one tap as a patient trigger to activate cueing. In one embodiment, the controller is customised to parameters specific to a patient for recognising taps. Preferably, the controller recognises a series of multiple taps as said patient trigger. In one embodiment, the controller recognises a series of two taps as said patient trigger.

In one embodiment, the controller recognises said taps if they comply with parameters of (a) latency, being a minimum time which must elapse between the first and the second tap being performed, (b) threshold, which is a minimum acceleration which must be detected before an acceleration spike is recognised as a tap, (c) time limit, which is the maximum time which can elapse from the acceleration signal exceeding the threshold to returning below the threshold, and (d) window, which is the time after the latency, by which time the subsequent tap must have crossed the threshold.

In another aspect, the invention provides a non-transitory computer readable medium comprising software code for performing the steps of a method of any embodiment when executed by a digital computer Additional Statements According to the invention, there is provided a gait management apparatus for a user suffering from a neurological disease displaying gait dysfunction, the apparatus comprising: at least one motion sensor, at least one cueing actuator or device with an electrical stimulation electrode, a controller configured to process motion sensing signals, to perform automatic detection of a gait dysfunction or potential gait dysfunction, and to activate said cueing actuator automatically upon said detection.

In one embodiment, the cueing actuators include a haptic actuator. In one embodiment, at least one actuator is arranged to be skin surface mounted. In one embodiment, at least one actuator is arranged to be implanted under a patient's skin. In one embodiment, at least one haptic actuator is arranged to be wrist-worn. In one embodiment, the apparatus further comprises a user interface and wherein the controller is configured to allow the user to activate cueing manually.

In one embodiment, the controller at least in part comprises a smartphone. In one embodiment, the controller is configured to activate one of haptic or electrical cueing in response to a manual cueing instruction. In one embodiment, the interface comprises a button for manual cueing activation. In one embodiment, at least one cueing actuator is configured to be worn.

In one embodiment, at least one cueing actuator is wirelessly linked with the controller.

In one embodiment, the controller is configured to detect freezing of gait occurrences and to activate cueing upon said detection. In one embodiment, the controller is configured to generate an output sensory level cueing signal to relieve or prevent gait abnormality. In one embodiment, the controller is configured to generate an output motor level cueing signal to relieve or prevent gait abnormality. In one embodiment, the controller is configured to generate cueing signals for surface-mounted electrodes. In one embodiment, the controller is configured to generate cueing signals for implanted electrodes.

In one embodiment, the controller is configured to apply electrical stimulation cueing to prevent the occurrence of freezing of gait when the controller senses that a patient is walking or has an intention to walk.

In one embodiment, the controller is configured to determine characteristics of a patient and to deliver electrical stimulation cueing customised to determined requirements of the patient. In one embodiment, said characteristics include skin impendence, and/or sensory threshold, and/or motor threshold, and/or pain threshold, and/or pain tolerance. In one embodiment, the controller is configured to apply cueing with a series of bursts until it automatically determines that a gait abnormality has ended.

In one embodiment, the processor is configured to apply electrical stimulation cueing at an intensity level which is insufficient for muscle contraction but sufficiently high to elicit a sensory response. In one embodiment, at least one cueing actuator comprises a wrist-worn haptic device such as a digital watch with haptic functionality for sensory stimulation.

In one embodiment, the controller is configured to determine if stimulation at a sensory level for cueing purposes is required or if stimulation at a motor level is required, and to provide output signals accordingly.

In one embodiment, the controller is configured to output stimulation signals with a pulse width of up to 1000 µs, and an inter-pulse interval of up to 100 µs. In one embodiment, the controller is configured to output stimulation signals with a pulse frequency of up to 60 Hz.

In one embodiment, the controller is configured to output stimulation signals for a maximum stimulation surface voltage of 68V. In one embodiment, the controller is configured to output stimulation signals for an implanted stimulation current range from 10 µA to 50 mA.

In one embodiment, the controller is configured to output stimulation signals with an envelope having characteristics of a ramp-up time of up to 5000 ms, an ON time of up to 10,000 ms, a ramp-down of up to 500 ms, and an OFF time of up to 5000 ms.

In various embodiments the invention provides a gait management apparatus for a user suffering from a neurological disease displaying gait dysfunction. The apparatus comprises: a controller, sensors (for example, accelerometers, gyroscopes and EMG) which may be worn externally on the person or implanted, and a cueing actuator(s). Cueing modality is in the form of an electrical or haptic (mechanical) cue, for electrical cueing electrodes for cueing delivery at least one anatomical site either on the skin surface or implanted just below the skin surface, a haptic cueing device worn at the wrist or other appropriate site. There may be an interface for coupling with electrical stimulation electrodes, a controller configured to receive sensing signals, a controller configured to allow the user to activate cueing manually, and a controller to process motion sensing signals to activate cueing automatically at the electrodes or haptic cue site to relieve or prevent a gait abnormality. An interface (such as a smartphone) may be provided to control, change, store and transmit required cueing parameters.

The apparatus may have some or all of the following features:
- An actuator for user self-actuation (manual activation) of electrical cueing.
- An actuator for user self-actuation (manual activation) of haptic cueing.
- The actuator comprises a device configured to be worn on the person.
- The cueing device is wirelessly linked with the processor.
- The motion sensing module is configured to detect freezing of gait occurrences and to activate cueing upon said detection.
- The controller is further configured to generate an output sensory level cueing signal to relieve or prevent gait abnormality.
- The controller is further configured to generate an output motor level cueing signal to relieve or prevent gait abnormality.
- The controller is configured to generate cueing signals for surface-mounted electrodes.
- The controller is configured to generate cueing signals for implanted electrodes
- The processor is programmed to apply electrical stimulation cueing to prevent the occurrence of freezing of gait when the controller senses that a patient is walking or has an intention to walk.
- The controller is configured to determine characteristics of a patient and to deliver electrical stimulation cueing customised to determined requirements of the patient, and these characteristics may include skin impendence, sensory threshold, motor threshold, pain threshold and pain tolerance.
- The processor is configured to apply stimulation (electrical or haptic) with a series of bursts until it automatically determines that a gait abnormality has ended.
- The processor is configured to apply electrical stimulation at an intensity level which is insufficient for muscle stimulation but sufficiently high to elicit a sensory response.
- The processor is operating on a mobile platform such as Apple iPhone™ and via the Apple Watch applies haptic (mechanical vibrations) cueing at an intensity level which is sufficient for sensory stimulation.
- The processor is operating on a mobile device such as Android™, Android Wear™ or Microsoft™ platforms and via a smartwatch applies haptic (mechanical vibrations) cueing at an intensity level which is sufficient for sensory stimulation.
- The processor is configured to determine if stimulation at a sensory level for cueing purposes is required or if stimulation at a motor level is required and provides output signals accordingly.
- The processor is configured to output stimulation signals with a pulse width of up to 1000 µs, and an inter-pulse interval of up to 100 µs.
- The processor is configured to output stimulation signals with a pulse frequency of up to 60 Hz.
- The processor is configured to output stimulation signals for a maximum stimulation surface voltage of 68V.
- The processor is configured to output stimulation signals for an implanted stimulation current range from 10 µA to 50 mA.
- The processor is configured to output stimulation signals with an envelope having characteristics of a ramp-up time of up to 5000 ms, an ON time of up to 10,000 ms, a ramp-down of up to 500 ms, and an OFF time of up to 5000 ms.

Software and algorithms run on the software that may be used to perform the various functions of the motion sensor, the controller, the processor, the cueing actuator, and other elements of the systems and methods described in the present application are disclosed in C. Ahlrichs et al., "Detecting Freezing of Gait With a Tri-axial Accelerometer in Parkinson's Disease Patients," *Med. Biol., Eng. Compu.* (2016) 54:223-233; and C. Perez-Lopez et al., Dopaminergic-induced Dyskinesia Assessment Based on a Single Belt-Worn Accelerometer," *Artificial Intelligence in Medicine*, 67 (2016) 47-56, the entire contents of which are incorporated herein by reference.

DETAILED DESCRIPTION OF THE INVENTION

Brief Description of the Drawings

The invention will be more clearly understood from the following description of some embodiments thereof, given by way of example only with reference to the accompanying drawings in which:—

FIG. 21 shows examples of somatosensory receptors in more detail, FIG. 22 shows the somatosensory receptors found in tendons and skeletal muscle (proprioceptors) the Golgi Tendon Organ and Muscle Spindle respectively, and FIG. 23 shows joint somatosensory receptors in a typical joint such as the knee joint;

DESCRIPTION OF THE EMBODIMENTS

Overview

A cueing system is described for the relief and prevention of freezing of gait (FOG) particularly for Parkinson's disease. It provides in various embodiments a cue in the form of a burst of electrical stimulus either on the skin surface or directly on a sensory and/or motor nerve when a FOG event (common with neurological diseases like Parkinson's disease) is detected. FOG can be detected automatically by the system using a range of sensors or when the user senses their FOG episode themselves, he/she can manually activate the system. The system may also provide a regular pattern of electrical pulses (acting as a cue) when the person is walking to prevent FOG occurring.

Figure 22:
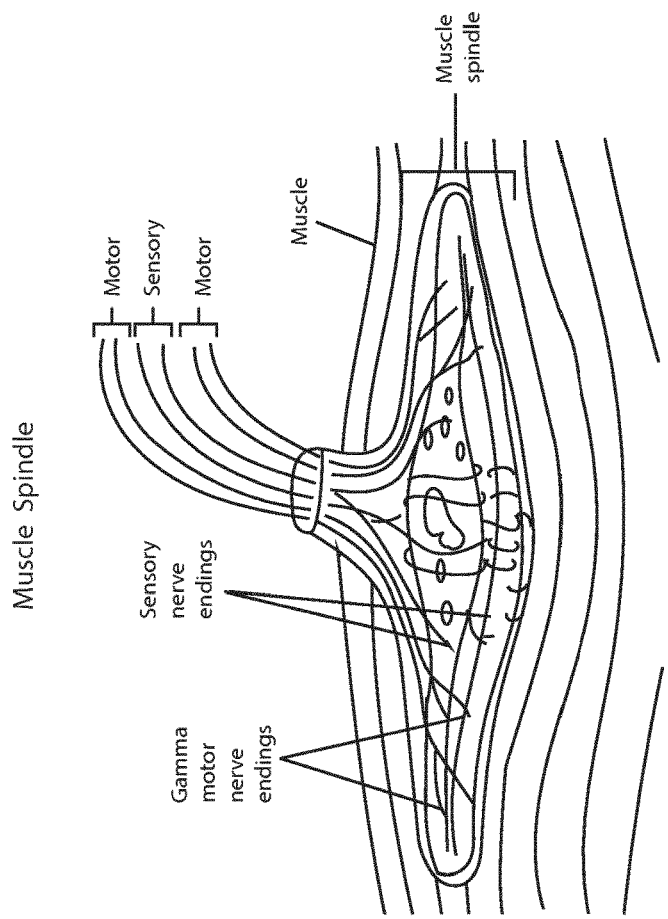
Figure 22:
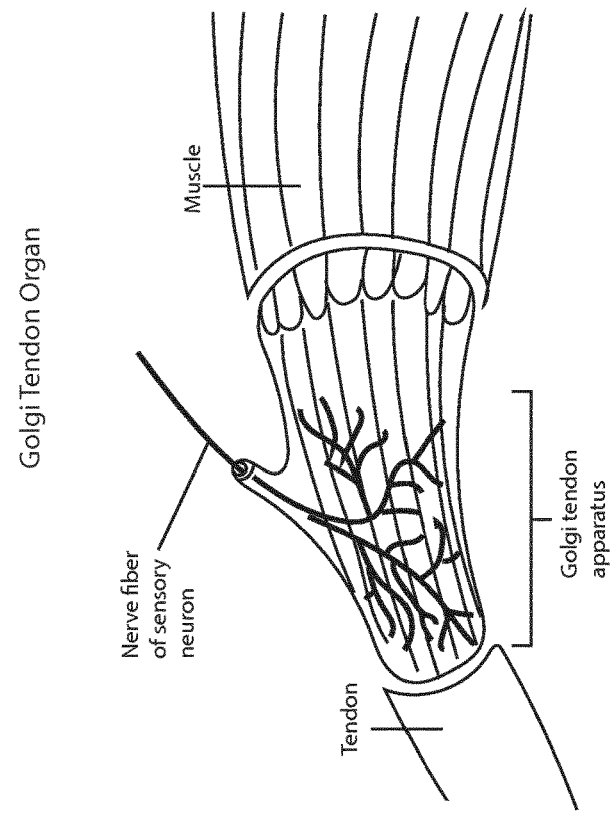
Figure 23:
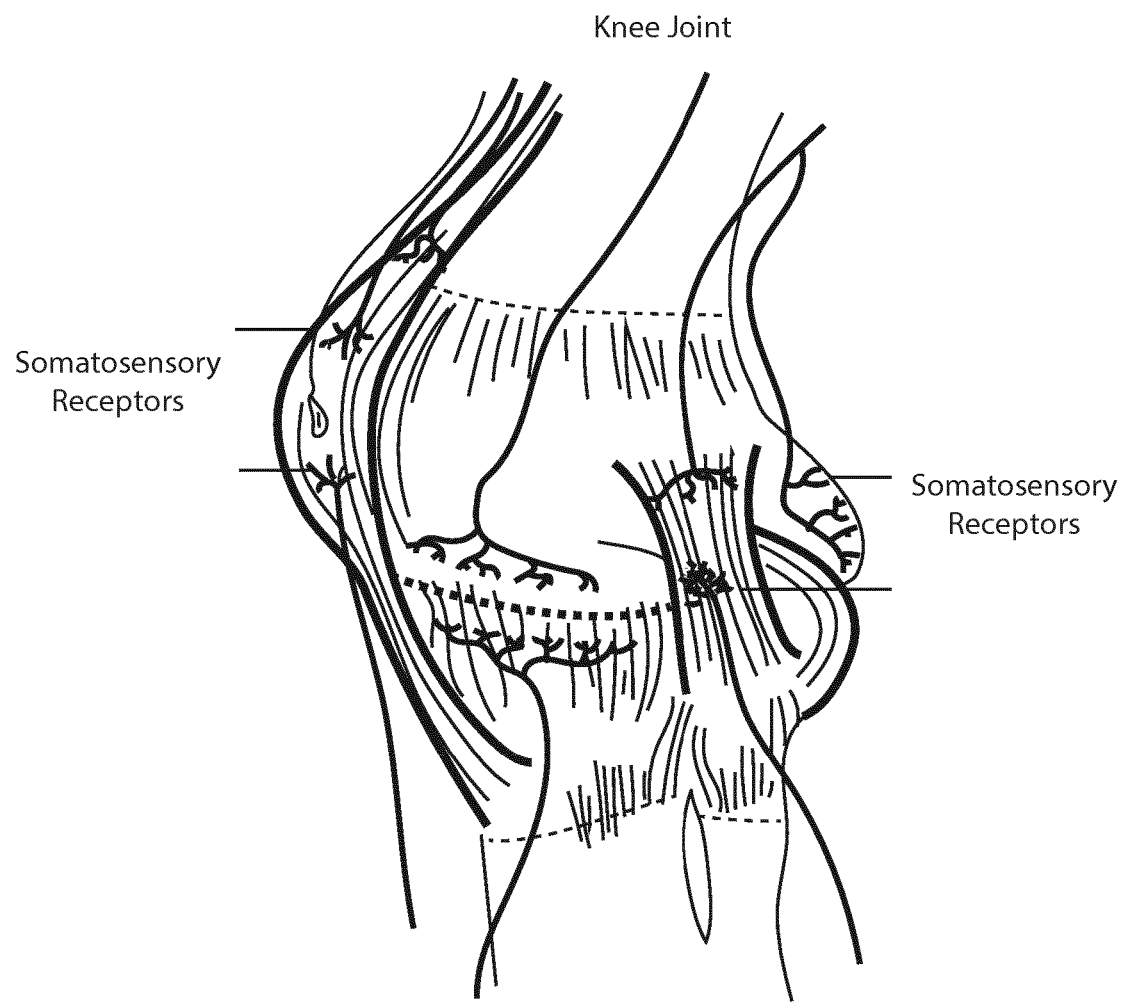
Figure 24:
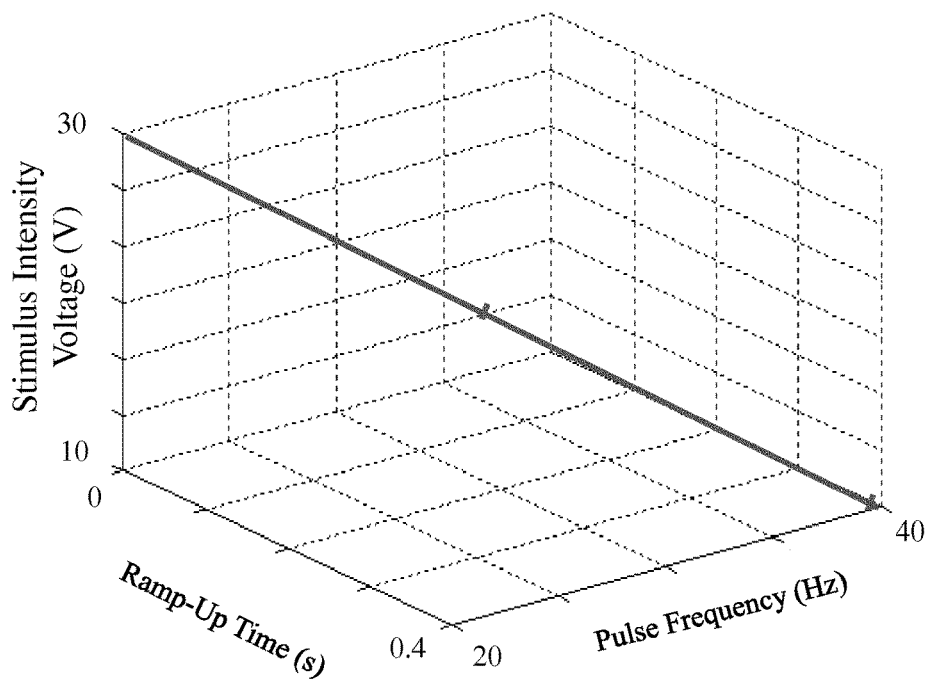
FIGS. 24 and 25 are 3D plots illustrating dynamic modification of cueing by following a line representing combinations of three parameters.
Figure 25:
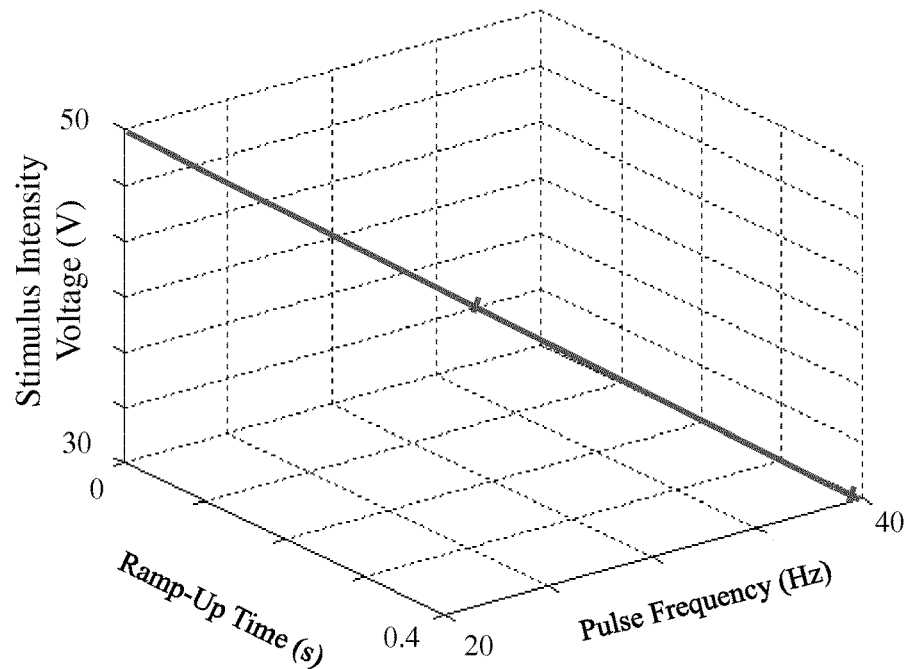
Figure 26:
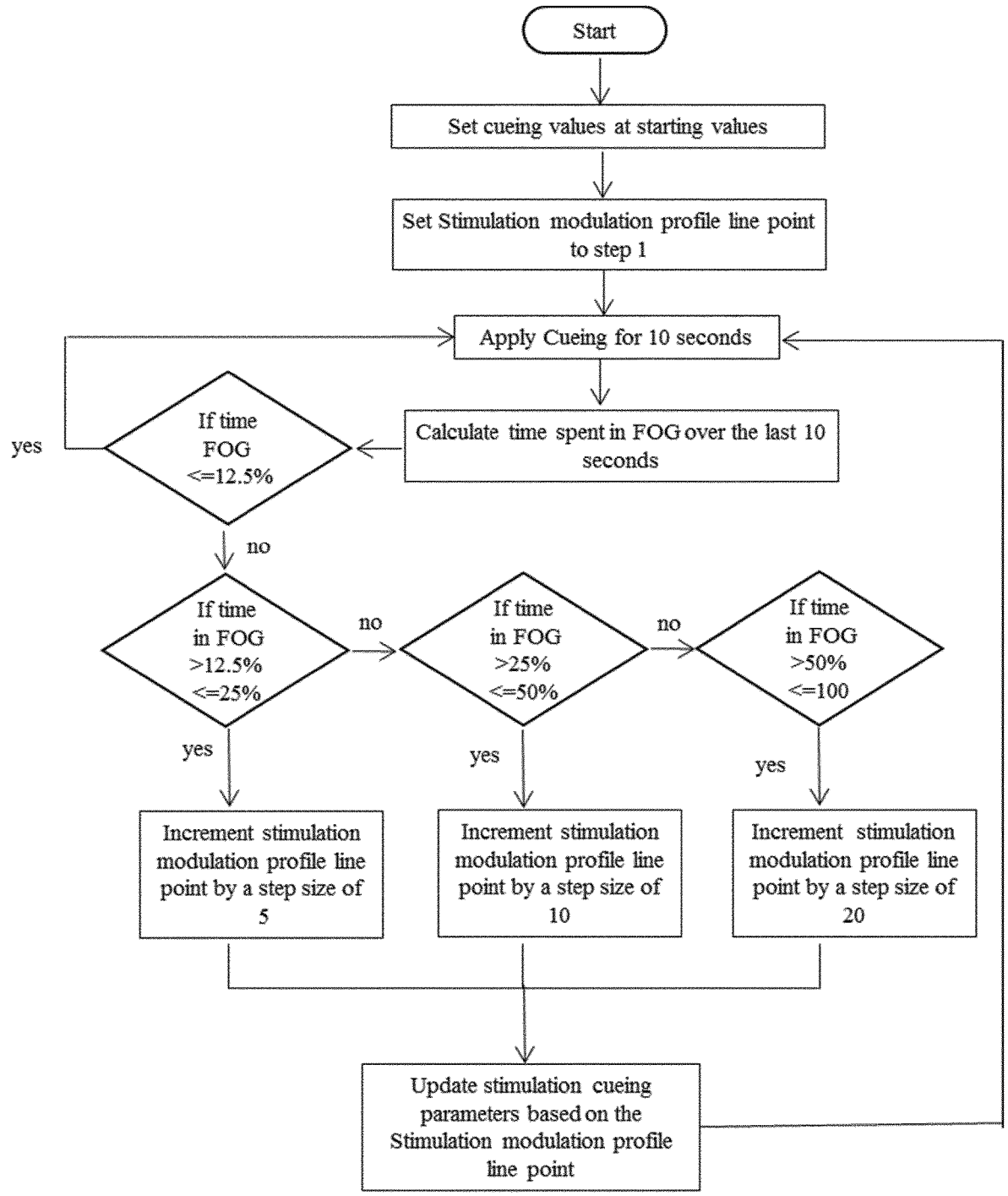
FIG. 26 is a flow diagram for operation of the controller for dynamic cueing modification.

FIGS. 1 to 19 inclusive and FIGS. 24 to 26 inclusive illustrate various embodiments, and FIGS. 20 to 23 illustrate a patient's anatomy which is responsive to cueing provided by the apparatus.

The somatosensory system is targeted in all cases and it represents several somatic sensation modalities such as cutaneous sensations (e.g. touch, temperature and pain) and proprioception sensations (e.g. muscle status (length/rate of change of length and tension) and joint angle). Each of these modalities and their sub-modalities (e.g. the cutaneous sensation of pain can be sharp, dull or deep) is represented by neurons that exhibit modality specificity. That is, when a specific somatosensory neuron is stimulated naturally (e.g., by touching the skin) or artificially (e.g., by electrical stimulation), the sensation perceived is specific to the neuron that is activated. Thus, a "touch" somatosensory neuron will naturally only respond to its adequate stimulus, which is touch and will not for example naturally respond to different stimulus, for example a change in skin temperature.

Figure 20:
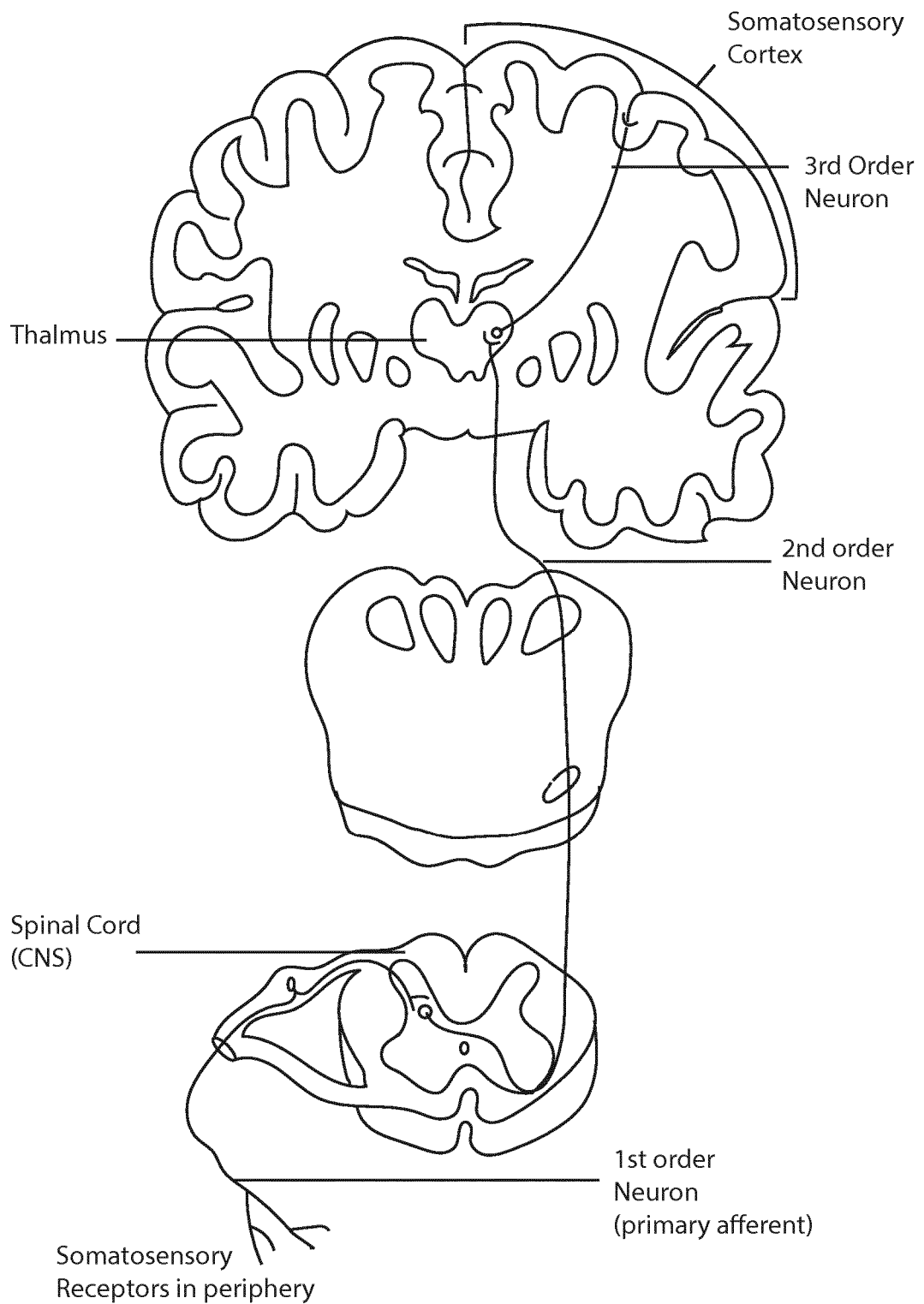
FIGS. 20 to 23 are diagrams illustrating anatomical and physiological components of the human somatosensory system to provide context to the invention, FIG. 20 showing the typical pathway from a peripherally located somatosensory receptor to the somatosensory cortex.

The somatosensory system is organised such that there is a chain of neurons starting at the sensory receptor and ending in the somatosensory cortex in the brain (FIG. 20).

The first neuron in this chain of neurons is referred to as the primary afferent neuron and is organised such that its axon and cell body are part of the peripheral nervous system. An afferent neuron is one which carries information from the periphery to the CNS. In contrast an efferent neuron carries information from the CNS. These peripheral nerves thus contain the specific sensory receptors for each modality and travel between the skin, muscles, tendons or joints and the central nervous system.

Figure 21:
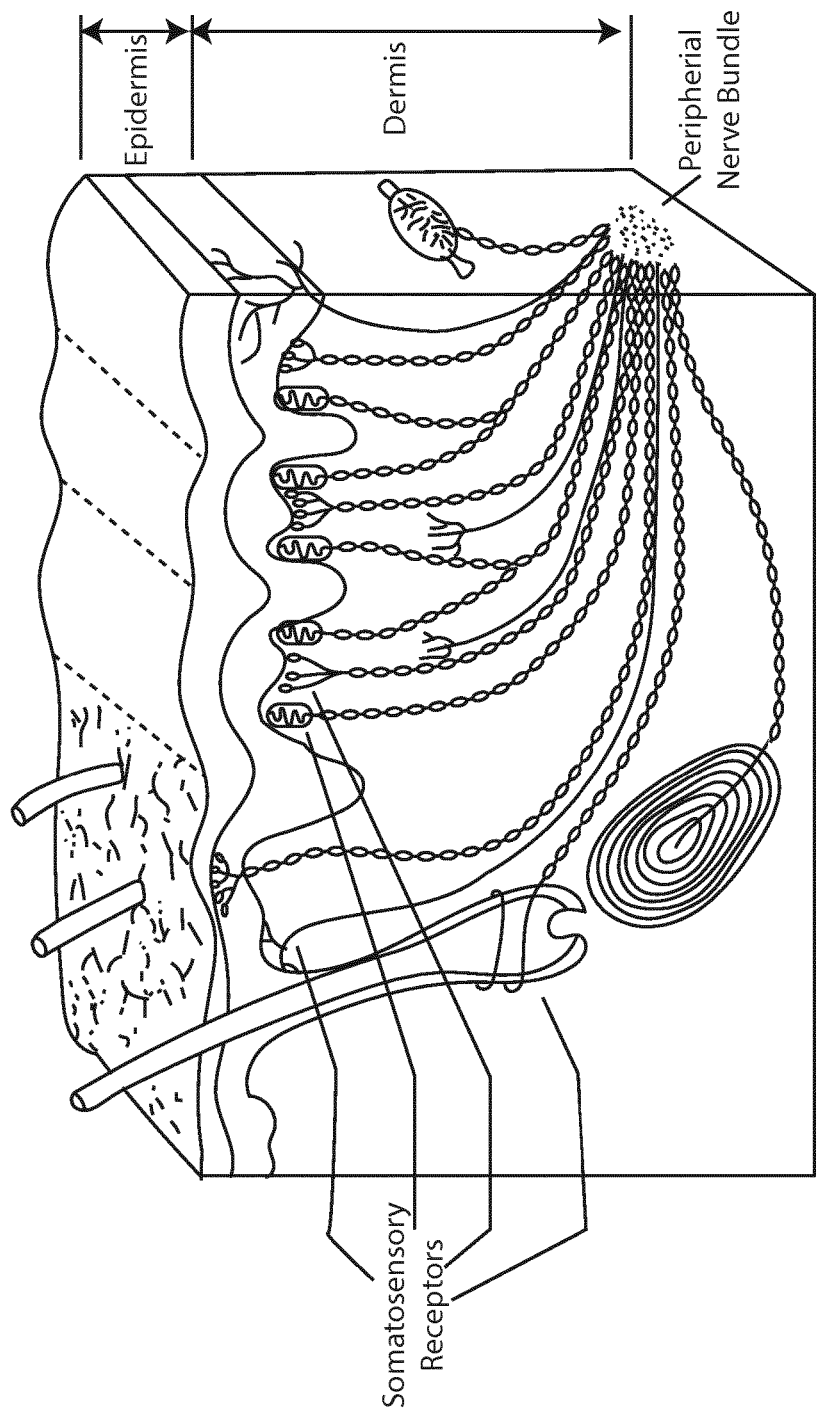

The peripheral nerve bundle pathways carrying the skin somatosensory information to the CNS, form a nerve bundle just below the skin surface, which allows for the convenient artificial activation of multiple modalities using appropriate electrical stimulation parameter values (amplitude, pulse width, inter-pulse interval, frequency, ramp up time, ramp-down, ON-time and OFF-time) delivered using either skin surface electrodes or implanted electrodes in proximity to the nerve bundle (FIG. 21).

Proprioceptors are located in muscles, tendons, joint ligaments and in joint capsules (FIGS. 22 and 23).

In skeletal muscle, there are two types of proprioceptors associated with skeletal muscle namely the muscle spindles and Golgi tendon organs. The muscle spindles are proprioceptors which monitor muscle length and its rate of change and signal the rate of change in muscle length by changing the discharge rate of the afferent nerve action potentials. The Golgi tendon organ monitors changes in muscle tension. Thus any stimulus that results in muscle contraction across the continuum from a simple twitch response to a maximal contraction resulting in a change in the joint angle, will result in the activation of additional (additional to the cutaneous somatosensory modalities) somatosensory sensory signals, proprioception somatosensory signals.

These proprioception somatosensory signals arise in response to muscle activation, thus acting as a potential cue to relieve or prevent FOG.

Additionally, within the joints, there are encapsulated nerve endings similar to those found in the skin, as well as numerous free nerve endings which fire in response to changes in joint angle. Thus electrical stimulation of skeletal muscle which results in muscle contraction across the continuum from a simple twitch response to a maximal contraction will produce somatosensory proprioceptive inputs to the CNS that may be effective cues for the relief and/or prevention of FOG. In this invention there are two distinct anatomical components involved: the Peripheral Nervous System (PNS) and the Central Nervous System (CNS). Arising from artificial electrical stimulation of the PNS, sensory action potential signals travel from the PNS to the CNS where this sensory input gives rise to a natural motor response (re-commence walking in the case of FOG relief or maintain walking in the case of FOG prevention).

The artificial electrical stimulation (using either surface or implanted means) of the PNS is where electrical stimulation is used to trigger either a one-step or a two-step somatosensory response.

In a one-step response, electrical stimulation triggers activation of a sensory nerve or nerves and the action potentials from these afferent sensory nerves travel to the CNS where they are processed. This one-step response is a cutaneous multi-modal somatosensory response from the PNS.

In a two-step response, Step one sees artificial electrical stimulation triggering activation of a motor nerve or nerves (efferent nerves) and the corresponding skeletal muscle is activated (albeit at a level below that required to produce a functional contraction). Step 2 then sees the firing of sensory receptors in the activated skeletal muscle (muscle spindle) or tendon (Golgi tendon organ) in response to this skeletal muscle activation. The action potentials from these sensory nerves (afferent nerves) then travel to the CNS where they are processed. The second step of this response is a multi-modal somatosensory response from the PNS.

The CNS is where the artificially induced sensory action potentials received from the PNS via afferent pathways, are acted on giving rise to a natural motor response (re-commence walking in the case of FOG relief or maintain walking in the case of FOG prevention).

Systems of the invention in various embodiments perform electrical stimulation to artificially cause multi-modal somatosensory stimulation, and different cueing modalities are triggered either individually or in combination through the use of appropriate electrical stimulation parameters. Advantageously, the processor is configured to dynamically choose how to perform stimulation, and this is performed according to the patient's individual characteristics. Preferably, the stimulation is somatosensory up to a level of non-functional movement, Hence the cueing can be sufficient to maybe cause muscle contraction, but will not be sufficient to aid in the execution of a functional movement. Ranges of appropriate electrical stimulation parameters include but are not limited to: pulse widths ranging from 0 μs up to 1000 μs, inter-pulse intervals ranging from Op up to 1000 μs, pulse frequencies ranging from 0 Hz up to 60 Hz, surface stimulation intensity voltages up to 100V, surface stimulation intensity currents up to 200 mA, implanted stimulation intensity currents ranging from 0 μA to 200 mA, stimulation signals with an stimulation intensity envelope having characteristics of a ramp-up time of up to 1000 ms, an ON time of up to 10,000 ms, a ramp-down of up to 1000 ms, and an OFF time of up to 10,000 ms.

The apparatus has at least one motion sensor, and at least one cueing actuator or device with a pair of skin surface electrical stimulation electrodes or a pair of implanted electrical stimulation electrodes positioned to trigger activation of peripheral motor or sensory nerves. The skin surface electrical stimulation electrodes may be wired, in which case the electrode is simply a passive electrode 'patch', or the electrode may be wireless, where it is an active electronic device that communicates wireless with the actuator as well as incorporating the passive electrode 'patch'. For stimulation of motor nerves it is preferred that it is up to and including a stimulation that results in a muscle contraction which will not be sufficient to aid in the execution of a functional movement. A controller is configured in hardware and software programming to process motion sensing signals, to perform automatic detection of a gait dysfunction or potential gait dysfunction, and to activate the cueing actuator automatically upon detection.

A functional muscle contraction is a biomechanical-task based muscle contraction which is achieved by enabling a muscle contraction of sufficient intensity as to facilitate a functional movement, for example hand grasping in upper limb rehabilitation or drop foot correction in lower limb stroke rehabilitation. In each of these cases the muscle is contracted to a level to facilitate a functional task through limb movement.

A non-functional muscle contraction is a muscle contraction where the intensity of contraction is across the full continuum from a twitch response up to but not including a muscle contraction which will aid in the execution of a functional movement.

There may be at least one electrical stimulation actuator which is arranged to be wrist-worn. The apparatus may have a user interface and the controller may be programmed to allow the user to activate cueing manually.

In some examples, the controller may be configured in hardware and/or software to perform cueing with a stimulation which does not directly cause a functional muscle contraction. However, for the purposes of relieving or preventing gait abnormality, the cueing is sufficient to to cause in the patient the full continuum of muscle contraction: from a simple twitch response of the skeletal muscle up to but not including a muscle contraction of sufficient intensity as would aid in the execution of a functional movement.

In several embodiments, the controller is configured to generate cueing signals at peripheral anatomical sites.

The controller in some examples determines characteristics of a patient and delivers electrical stimulation cueing customised to determined individualized requirements of the patient.

The cueing actuator may comprise a wrist-worn electrical stimulation device such as a digital watch with functionality for multi-modal somatosensory electrical stimulation in response to electrical stimulation of peripheral sensory nerve bundles in the vicinity of the wrist using skin surface electrical stimulation electrodes at the wrist or implanted electrical stimulation electrodes located internally in the vicinity of the wrist.

The controller of some examples determines in real time if for cueing purposes, and to generate an effective cueing signal, stimulation should be at a sensory level (sensory threshold being less than motor threshold) or at a motor level and to provide output electrical stimulation signals accordingly.

The sensors may for example be accelerometers, gyroscopes and EMG devices which may be worn externally on the person or implanted. There may be an interface for coupling with electrical stimulation electrodes. The controller may be configured to allow the user to activate cueing manually, and/or to activate cueing automatically to relieve or prevent a gait abnormality. An interface (such as a smartphone) may be provided to control, change, store and transmit required cueing parameters.

The controller is configured in various embodiments to:
apply electrical stimulation cueing to prevent the occurrence of freezing of gait when the controller senses that a patient is walking or has an intention to walk, and
determine characteristics of a patient and to deliver electrical stimulation cueing customised to the unique requirements of the patient, and these characteristics may include skin impendence, sensory threshold, motor threshold, pain threshold and pain tolerance.

The patient characteristics can be learned by logging and monitoring the motion sensor inputs and/or it can be inputted as a patient profile before use.

In the case of automatic, sensor-controlled FOG relief, the processor is configured to apply electrical stimulation with a series of bursts until it automatically determines that a gait abnormality has ended.

In the case of patient-activated FOG relief, the processor is configured to apply electrical stimulation with a predetermined number of bursts when instructed to do so by the patient.

The processor may be configured to apply electrical stimulation at an intensity level which is insufficient for muscle stimulation but sufficiently high to elicit a cutaneous multimodal somatosensory response from the PNS. The action potentials from these sensory nerves (afferent nerves) then travel to the CNS where they are processed and acted on giving rise to a natural motor response (re-commence walking in the case of FOG relief or maintain walking in the case of FOG prevention).

The processor may be configured to apply electrical stimulation at an intensity level which is sufficient for muscle stimulation, albeit at a level below that required to produce a functional contraction, giving rise to a multimodal somatosensory response from the PNS. The action potentials from these sensory nerves (afferent nerves) then travel to the CNS where they are processed and acted on giving rise to a natural motor response (re-commence walking in the case of FOG relief or maintain walking in the case of FOG prevention).

Ranges of appropriate electrical stimulation parameters include but are not limited to: pulse widths ranging from 0 μs up to 1000 μs, inter-pulse intervals up to 1000 μs, pulse frequencies ranging up to 60 Hz, surface stimulation intensity voltages up to 100V, surface stimulation intensity currents up to 200 mA, implanted stimulation intensity currents ranging up 200 mA, stimulation signals with an stimulation intensity envelope having characteristics of a ramp-up time of up to 1000 ms, an ON time of up to 10,000 ms, a ramp-down of up to 1000 ms, and an OFF time of up to 10,000 ms.

A system of the invention may comprises a body-worn surface electrical stimulation device and/or a minimally invasive implanted electrical stimulation device, such as an injectable micro-stimulator, both of which deliver electrical stimulation elicited cues under manual or sensor control, to either relieve FOG (when it is detected) through the delivery of short duration bursts of electrical stimulation or to prevent FOG through the delivery of repetitive regularly timed bursts of electrical stimulation during walking. The system is a low-cost, minimally invasive system that is capable of operating effectively in a wide range of environmental conditions as the user goes about their daily life.

With the invention the electrical stimulation is primarily delivered to elicit a multi-modal somatosensory response from the PNS which is in turn acted on by the CNS and it is through this multi-modal somatosensory response that cueing occurs. Thus, stimulation levels are such as to exceed the multi-modal somatosensory threshold but are not in many cases at the levels normally used for functional muscular contraction. We refer to this electrical stimulation as "Multi-modal Somatosensory Electrical Stimulation Cueing". With a surface electrical stimulation electrode implementation, Multi-modal Somatosensory Electrical Stimulation Cueing is achieving by delivering electrical stimulus through a pair of skin surface electrodes, which can be placed close to each other (typically between 0-15 cm apart) on the skin at a wide range of sites. These sites can be chosen using a combination of three criteria: (i) a location on the skin where there is enhanced somato-sensory sensitivity, (ii) a location on the skin where electrodes will be concealed by clothing, (iii) a location on the skin where connection to a body-worn (waist-worn or wrist-worn) electronic unit is facilitated by the location (on surface of the quadriceps or hamstrings muscles when the body worn electronic unit is worn on the waist, on the wrist when the unit is worn on the wrist).

Another embodiment of the invention involves the use of skin surface mechanical stimulation as a cueing mechanism, rather than electrical stimulation cueing. The mechanical vibration would be delivered via a system of vibration motors fitted on a wrist worn device so that skin surface of the wrist is mechanically stimulated in a controlled manner under user or sensor control. The haptic feedback mechanism on a digital watch could be adapted for this purpose with a watch haptic engine delivering the skin surface mechanical stimulation cueing on the skin surface at the wrist. The algorithms and methods of control for controlling the delivery of this mechanical stimulation would be identical to those described herein for controlling the delivery of Sensory Electrical Stimulation cueing as shown in FIG. 7, FIG. 8, FIG. 10, FIG. 11, and FIG. 12. The cueing system using this method of the invention would be in the form of an App for a digital watch and the sensing mechanism would use the built-in watch sensors such as accelerometers, gyroscopes, barometers and magnetometers as well as the sensors in the accompanying smartphone. The self-activation of the delivery of mechanical stimulation cueing would be triggered by the user making a characteristic swipe on the digital watch surface, which could be recognized by the App, or by the user using a double tap action on the surface of the watch. An example of the type of digital watch is the Apple Watch™.

For sensor control of the electrical stimulation device, a range of sensors can be used such as accelerometers, gyroscopes, and physiological sensing such as EMG. These sensors can be located at different anatomical sites on the surface of the body and mounted into enclosures to facilitate attachment of the sensor at this site. For example, sensors could be mounted in an enclosure fitted on the wrist and/or mounted in an enclosure fitted on the waist. These sensors can be implanted using minimally invasive implantation techniques (for example using injectable techniques).

The invention facilitates manual, direct user controlled activation of electrical cues (button press, tapping (single or double), capacitive sensing of touch) or automatic motion sense detection as possible mechanisms to activate the electrical stimulus actuator directly. The apparatus also allows for manual activation via a wireless communication enabled wrist-worn switch or smartwatch type device. Additionally, the apparatus has the capacity for the automatic detection of alterations in gait patterns including FOG via built-in accelerometers and gyroscopes. This apparatus provides an electrical stimulation elicited cue for gait correction and FOG relief to enable a user to get out of FOG (FOG relief) and also allows for continuous or adaptive electrical stimulation cueing to prevent FOG occurring in real-time.

The apparatus can be deployed to deliver electrical stimulus to a range of anatomical sites. One manifestation for example of our invention involves the use of the actuator (body-worn wireless communication enabled stimulator device) worn on the waist connected via a wired connection to a pair of skin surface electrodes positioned on the skin over the quadriceps or hamstrings muscle. In the event that a FOG episode is experienced by the user, they can press a button on a wireless communication-enabled wrist-worn device, which triggers activation of the electrical stimulus actuator to relieve the FOG. The apparatus offers a highly significant contribution to PD healthcare in improving quality of life through gait correction, FOG relief and FOG prevention and contributing to less frequent hospitalization by reducing falls.

The apparatus is capable of non-invasively, automatically or directly under user control, supporting gait correction and/or gait facilitation in Parkinson's disease patients by means of an advantageous electrical cueing or mechanical cueing modality.

The apparatus carries out this cueing function in real time, as the user goes about their daily life and provides a mechanism for both FOG relief and FOG prevention. The level or intensity of electrical/mechanical stimulus used for each patient can be adjusted within custom-defined limits locally at the device level or can be adjusted remotely over the Internet possibly by a clinician responsibly for the persons care. The apparatus can be used in a wide variety of environments with equal effectiveness. Examples of use include in the users' home where gait disturbances and FOG events frequently occur as the user passes through doorways or when moving along a corridor. The apparatus can also be used outside the home and importantly, unlike other cueing systems, is unaffected by ambient light or noise.

The primary function of the apparatus is to provide an electrical cue (sensory or motor) or mechanical (sensory) upon occurrence of a gait irregularity or to prevent that gait irregularity occurring in the first place.

Apparatus Examples

Figure 1:
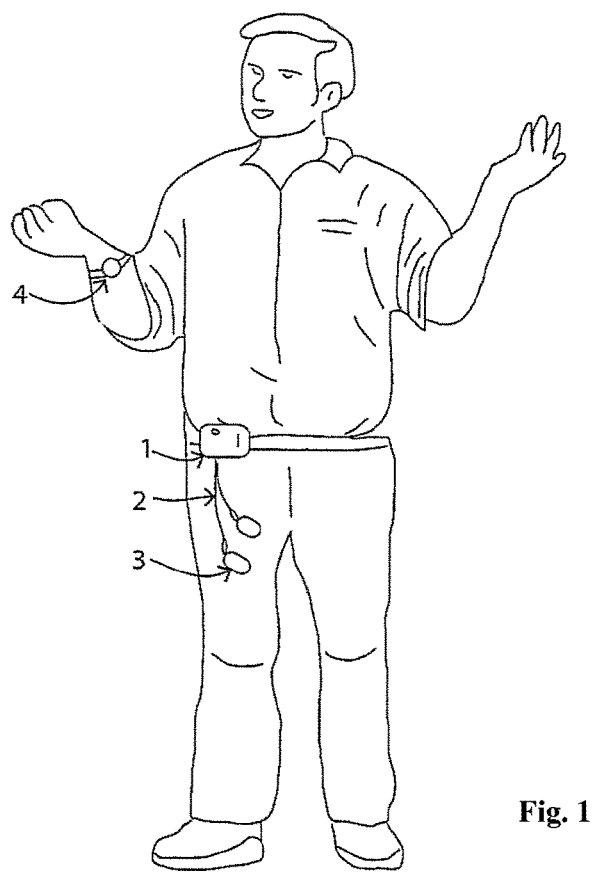
FIG. 1 is a diagram illustrating positioning of components of a system or "apparatus" of the invention on a patient.
Figure 2:
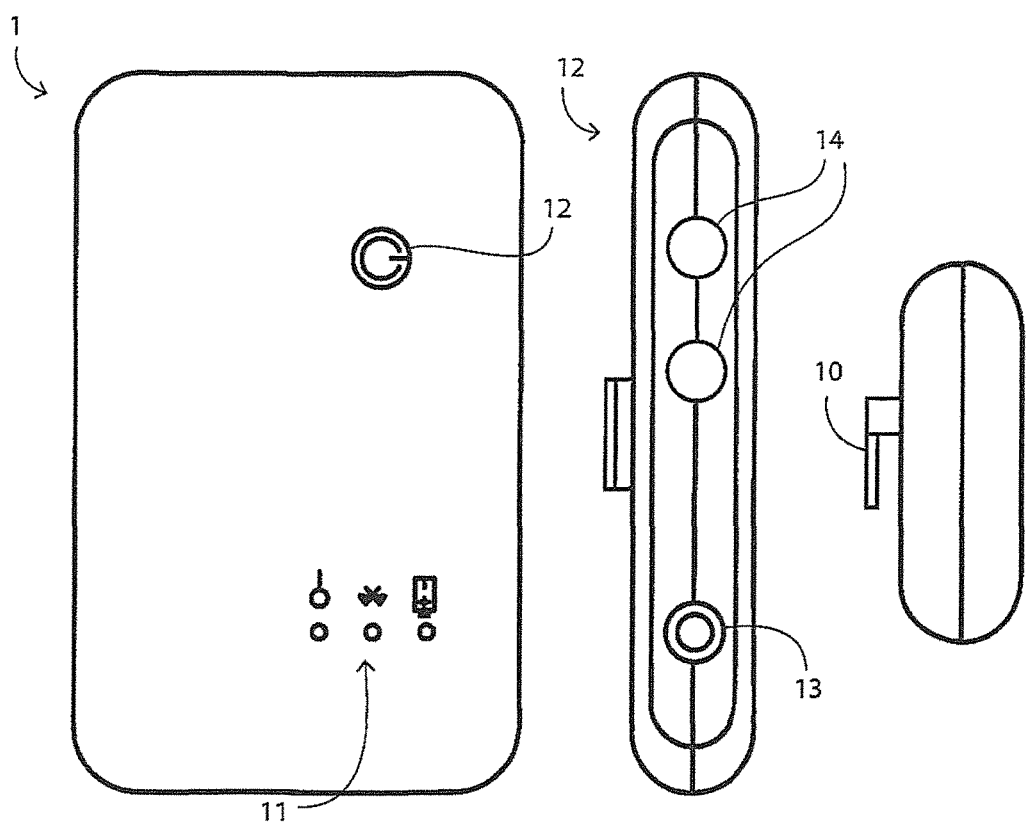
FIG. 2 is a set of front, plan, and side views of a control unit of the system.

In one embodiment the apparatus has a waist-worn electrical stimulation unit 1, connected by cables 2 to at least one pair of surface electrical stimulation electrodes 3 placed on the skin surface. Additionally, a wireless wrist worn accompanying device 4 can be employed with or without a smartphone. These components are shown in FIGS. 1 and 2.

The control unit 1 is worn attached to a belt or can be placed in a custom belt for easy placement at the waist. The control unit is connected via a cable running under the clothing to a pair of electrodes placed directly on the surface of the skin, the quadriceps in this case. The wrist worn companion device 4 is also shown and can be used for manual activation of cueing.

The unit 1 has a belt clip 10, status LEDs 11, an ON/OFF button 12, and output jacks 14 for stimulus delivery.

Apparatus Architecture and Manual Activation

Figure 3:
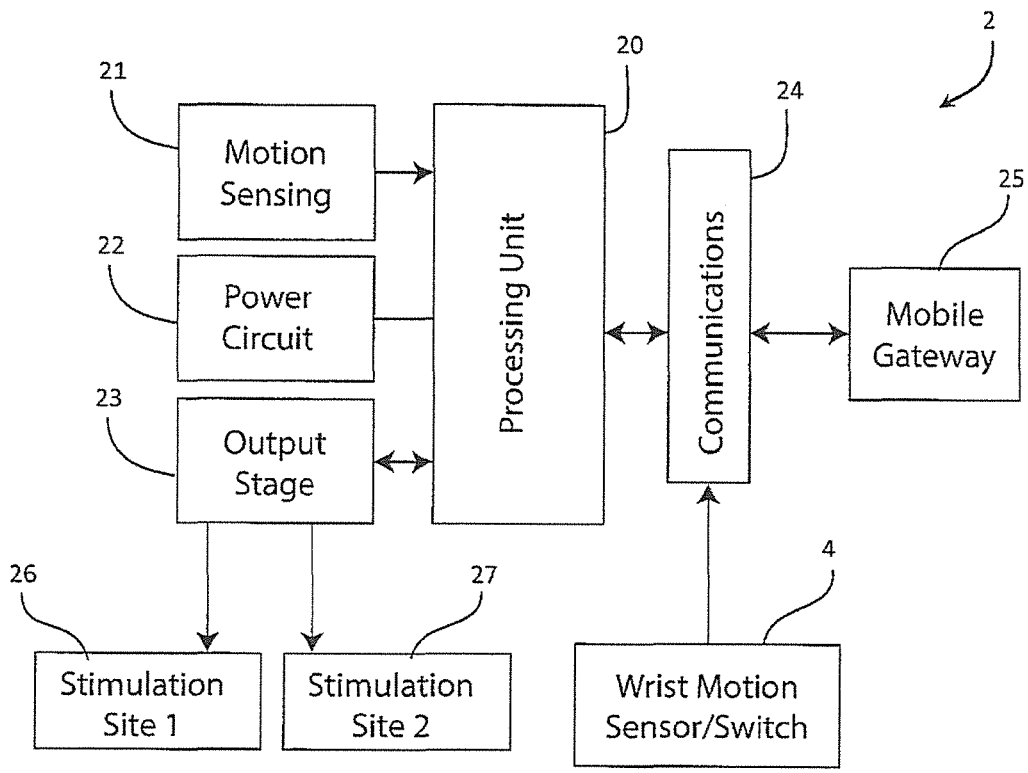
FIG. 3 is a block diagram of the system.

Referring to FIG. 3, the apparatus has a processing unit 20 linked with at least one motion sensor 21, an output stage 23, a communications module 24 and companion devices. The processor 20 uses the motion sensors for gait assessment and manual activation of cueing depending on the configuration.

For gait disturbance detection, the motion sensors 21 capture gait information and the processing unit determines if a gait disturbance (for example a FOG episode) is present. When a gait disturbance is confirmed from the data collected by the motion sensors, electrical cueing is activated. Alternatively manual activation of cueing can be achieved when the motion sensors capture a user specific tapping action on the control unit enclosure, which generates an interrupt signal. The interrupt signal is passed to the processing unit and electrical cueing is activated. Manual activation can also be achieved through the wrist-worn companion device 4. A simple tap or signature motion can be detected at the wrist and wireless transmitted to the processing unit in the waist worn unit whereupon electrical cueing is activated. The wrist worn unit can also be a simple ON/OFF switch, which is pressed by the patient or a capacitive touch sensitive area which is touched by the patient when they require cueing. In its most simple form of cueing, where a body worn unit is used, the apparatus delivers a burst of electrical stimulus to a skin surface site. Typical sites include the skin over the major muscle groups of the lower limbs (FIG. 4), the wrist, or ear lobe.

Lower Limb Stimulation

Figure 4:
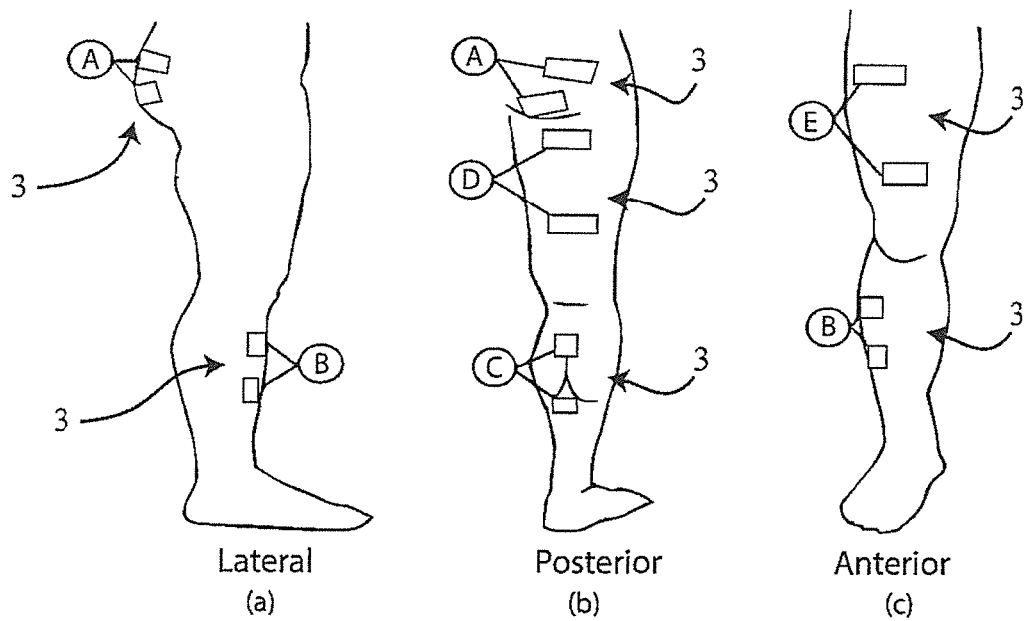
FIGS. 4(*a*), (*b*), and (*c*) are diagrammatic views showing possible locations of surface stimulation electrodes of the system.

FIG. 4 shows electrical stimulation cueing sites of the lower limbs. All electrodes are placed in pairs over the desired muscle group and connected back to the control unit. Muscle groups include, A gluteus maximus, B tibialis anterior, C soleus, D hamstrings and E quadriceps. While the electrodes are placed over the muscle groups, the intention is not to deliver sufficient stimulus to trigger contraction of the muscle, instead stimulus is delivered at an intensity level, which elicits a sensory response. We refer to this specifically as Sensory Electrical Stimulation Cueing, whereas when cueing is achieved through contraction of a muscle and limb movement, we refer to this as Motor Electrical Stimulation Cueing.

Figure 5:
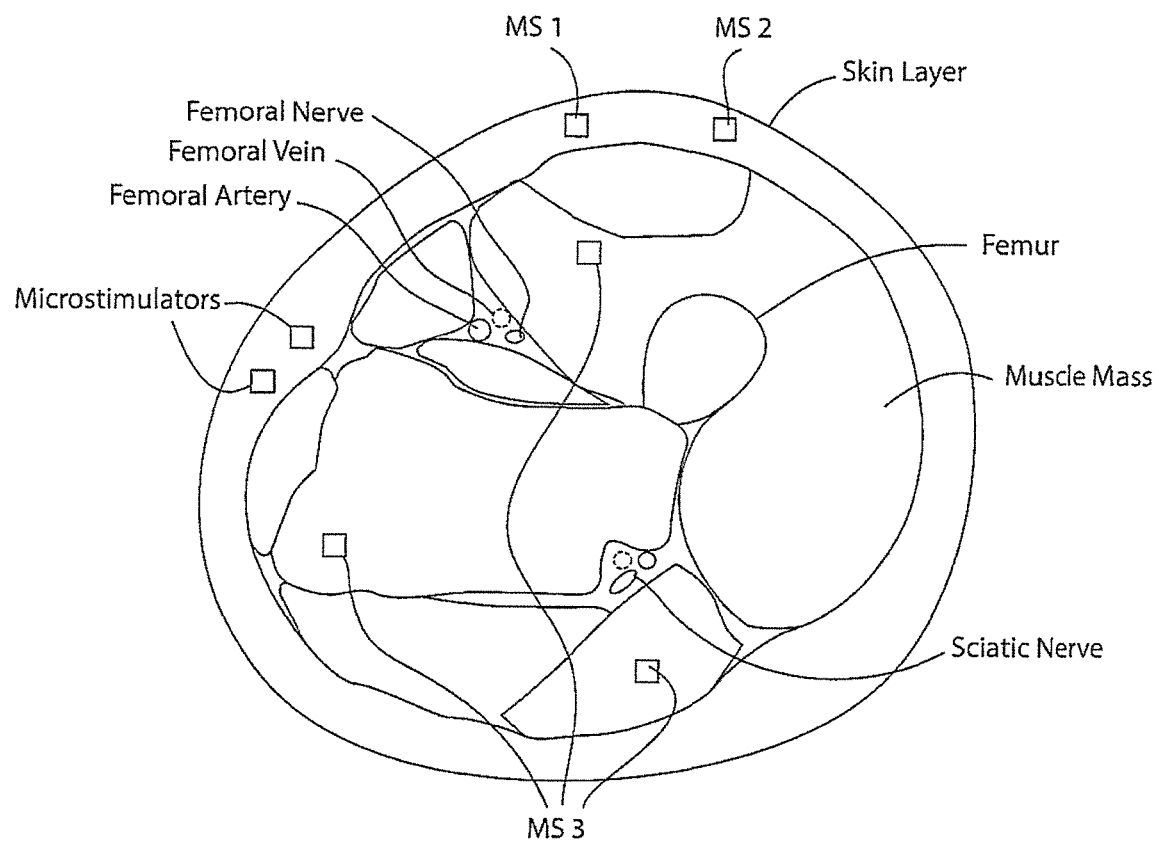
FIG. 5 is a diagram showing a cross-section of a human upper leg with sensory receptors in the skin.

Electrical stimulation can be applied using either surface techniques (electrodes on the skin surface) or implanted techniques (electrodes internal to the body). Electrical stimulation can be applied using two modalities: Motor Electrical Stimulation—the stimulus intensity is of sufficient intensity to trigger activation of motor neurons resulting in muscle contraction or Sensory Electrical Stimulation—the stimulation intensity is of sufficient intensity to trigger activation of sensory neurons giving rise to sensations normally attributed to the activation of sensory end organs—but the stimulation intensity is not sufficient to trigger motor activation. Neural activation from electrical stimulation through depolarization is dependent on the neuron's diameter and its proximity to the stimulation source (FIG. 5). The larger the axon diameter of the neuron, the lower its threshold of excitability, The greater the distance of an axon from the stimulation source the lower the depolarisation current at the neuron site.

Sensory neurons of the skin, while smaller in diameter than motor neurons are normally orders of magnitude closer to the skin surface than the motor nerves. Propagation of current flow from skin surface electrical stimulation electrodes is such that for a given electrical stimulation intensity the level of depolarization will be higher at the more superficial sensory neurons than at the deeper larger motor neurons. As stimulation intensity at the skin surface is increased the nerves associated with the sensory organs fire first—the stimulation intensity at which this occurs may be called the "Sensory Threshold". Continuing to increase the stimulation intensity will eventually result in the deeper motor nerves being triggered—the stimulation intensity at which this occurs is the "Motor Threshold". If the Motor Threshold has been exceeded, then clearly the Sensory Threshold has also been exceeded. Thus when the apparatus carries out motor FES stimulation it is in fact carrying out both motor FES stimulation and sensory FES stimulation.

We have carried out extensive testing of both sensory and motor electrical stimulation cueing in PD patients and it is very well tolerated by PD patients and highly effective as a cueing mechanism.

Motor electrical stimulation results in muscle contraction, and this can be used for two purposes: as a cueing mechanism as the contraction of the muscle and movement of the limb will provide a cue to the user through the mechanism of somatosensory proprioception signals travelling to the CNS from the PNS in response to muscle contraction, and also as a means to move a limb artificially and thus provide a mechanism for gait correction.

The rationale for placing the stimulation electrodes on the skin surface over the muscles is that the electrodes can ultimately have a dual function and when required deliver stimulation at a sensory level for cueing purposes but if required also stimulus can be delivered at a level which will directly via the efferent nerves cause a functional muscle contraction, which may also assist in overcoming gait disturbances using a different modality, for example contraction of the quadriceps muscle to extend the knee if required.

Stimulation Waveform

Figure 6:
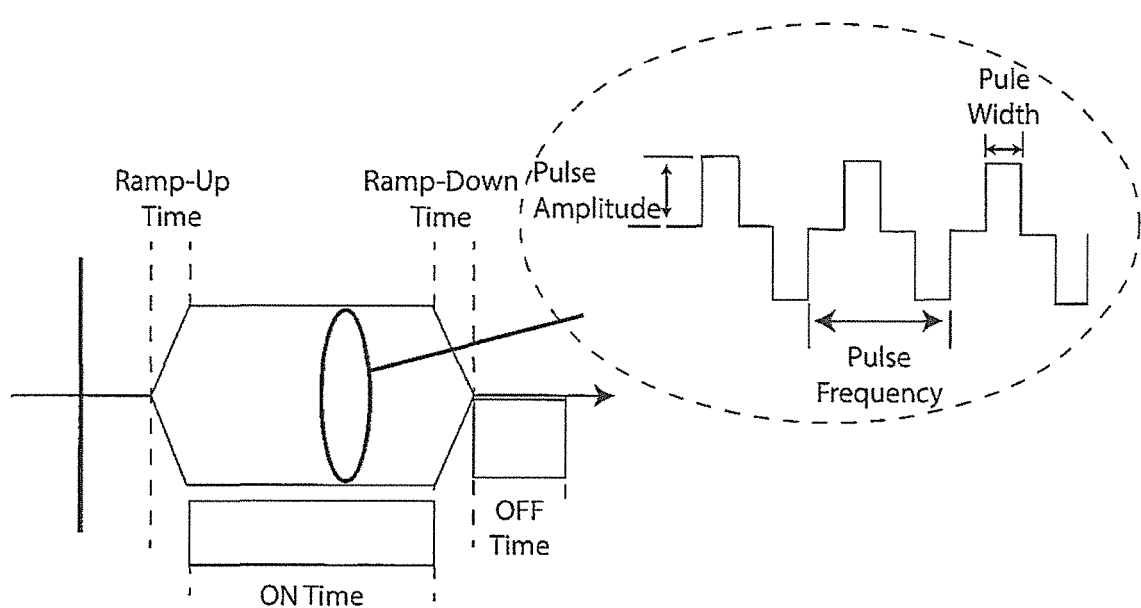
FIG. 6 is a plot illustrating a single electrical stimulation burst.
Figure 7:
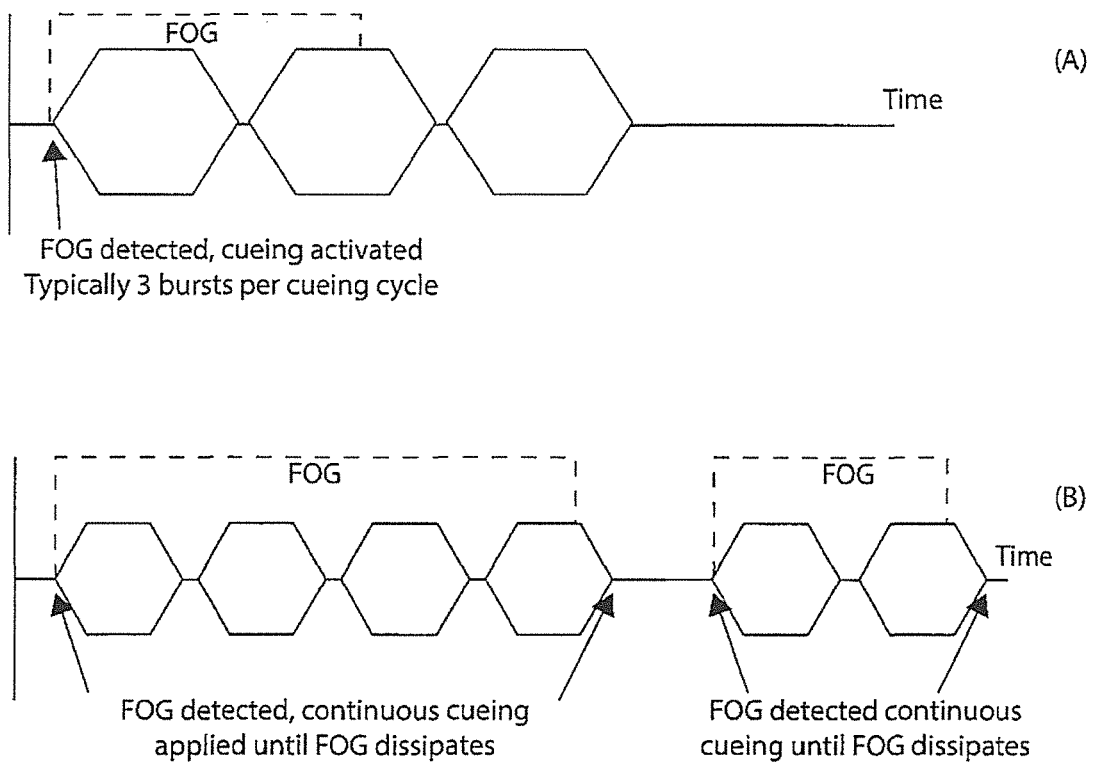
FIG. 7 is a pair of plots, (A) burst cueing activation in response to FOG detection, in which a typical burst consists of 3 stimulus bursts, (B) continuous stimulation applied while a FOG episode is present.

In some embodiments, for all cases of cueing, bipolar (biphasic) pulse stimulation waveforms are used, which allow for neural stimulation without causing tissue damage. These stimulus waveforms are characterized by three main parameters, pulse frequency, pulse amplitude and pulse width. The waveforms are delivered in short envelope bursts. Each envelope is defined by, Ramp-Up Time, ON Time, Ramp-Down Time and OFF time as shown in FIG. 6. The amplitude, inter-burst frequency and intra-burst pulse frequency can be unique and customized to each user for maximum clinical benefit. Furthermore the inter-envelope frequency and number of bursts can be predefined depending on user requirements.

Typical values are a pulse width of 350 µs, inter-pulse interval of 100 µs, pulse frequency of 36 Hz, and for surface stimulation a maximum stimulation voltage of 68V and for implanted stimulation intensity ranges from 10 µA to 50 mA of stimulation.

All these values are adjustable within defined ranges of appropriate electrical stimulation parameters including but are not limited to: pulse widths ranging from 0 µs up to 1000 µs, inter-pulse intervals ranging from 0 µs up to 1000 µs, pulse frequencies ranging from 0 Hz up to 60 Hz, surface stimulation intensity voltages up to 100V, surface stimulation intensity currents up to 200 mA, implanted stimulation intensity currents ranging from 0 µA to 200 mA, stimulation signals with an stimulation intensity envelope having characteristics of a ramp-up time of up to 1000 ms, an ON time of up to 10,000 ms, a ramp-down of up to 1000 ms, and an OFF time of up to 10,000 ms.

In another embodiment, the ranges are a pulse width of up to 1000 µs, inter-pulse interval of up to 100 ms, pulse frequency of up to 60 Hz and surface voltages of up to 68V and current of 10 µA to 50 mA. An example envelope has characteristics of a ramp-up time of 100 ms, ON time of 1000 ms, ramp-down of 100 ms, and an OFF time of 100 ms. All of these values are adjustable within defined ranges of ramp-up time of up to 5000 ms, ON time of up to 10000 ms, ramp-down of up to 5000 ms and an OFF time of up to 5000 ms.

Cueing Stimulation Profiles

The various embodiments of the present invention provide a method of correcting gait disturbance, relieving FOG and preventing FOG in a number of configurable setups depending on user preference, capabilities and clinical requirements. The electrical cueing is delivered in one of two modes depending on the configuration and user needs or preference. Stimulation can be delivered in Burst or Continuous mode. Both modes can be manually or automatically activated.

FOG Relief

In one embodiment the user is set up for automatic FOG relief with Burst mode cueing. In this configuration the motion sensor block monitors gait parameters. If FOG is detected, a burst of electrical stimulation of predefined duration is delivered (FIG. 7(A)). In another embodiment, the user is set up for automatic FOG relief and Continuous mode cueing. In this configuration the motion sensor block monitors gait parameters. If FOG is detected a continuous block of electrical stimulation is delivered (customizable frequency, for example 1 burst per second) until the FOG is relieved (FIG. 7(B)).

Figure 8:
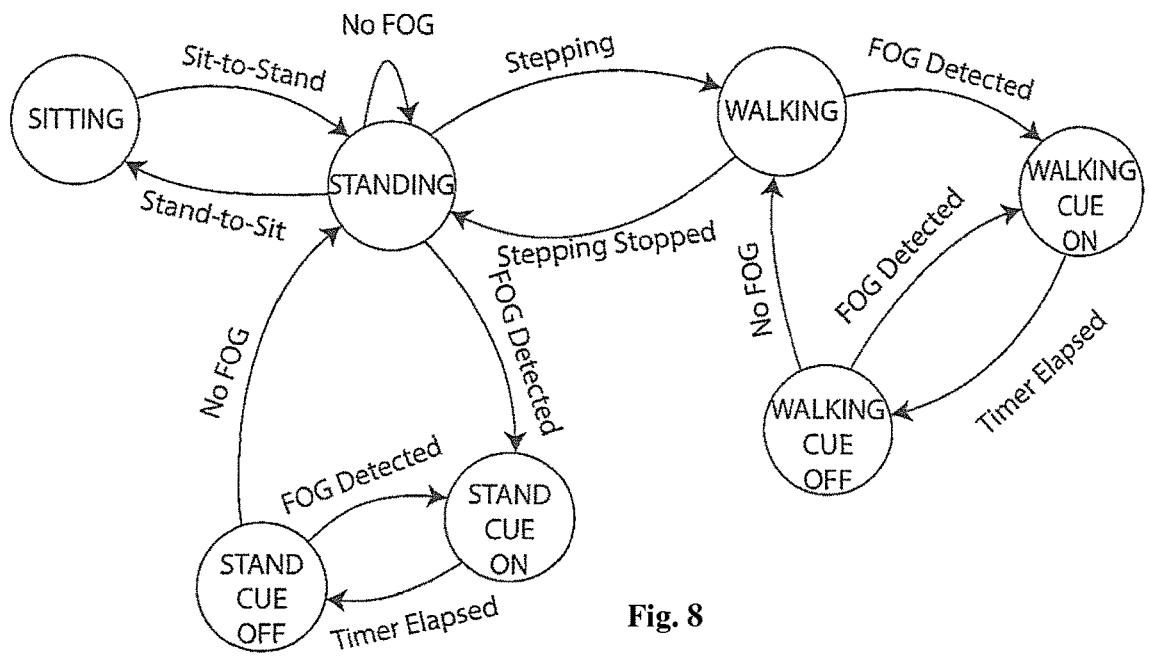
FIG. 8 is a diagram showing state transitions for FOG relief using electrical cueing in which the user starts in the sitting state.

The activation of the cueing system for FOG relief can be represented by a state transition diagram (FIG. 8).

Figure 9:
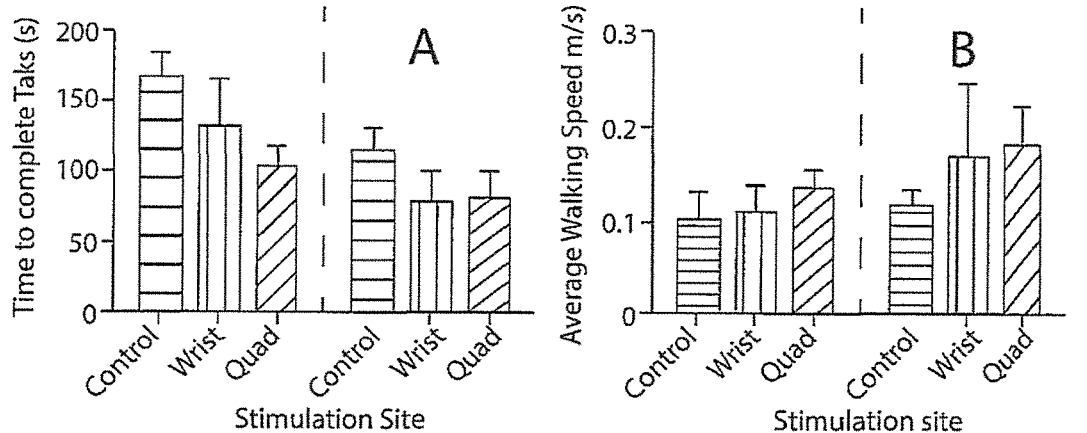
FIG. 9 is a set of plots A, B, and C, in which (A) plots effect of continuous cueing on time to complete a 14 meter walking task where cueing was applied at one of two sites when FOG was detected, (B) plots effect of continuous cueing on average walking speed over a 14 meter walking task where cueing was applied at one of two sites when FOG was detected, and (C) plots effect of continuous cueing on time spent in FOG state over the duration of a 14 meter walking task where cueing was applied at one of two sites when FOG was detected.
Figure 9:
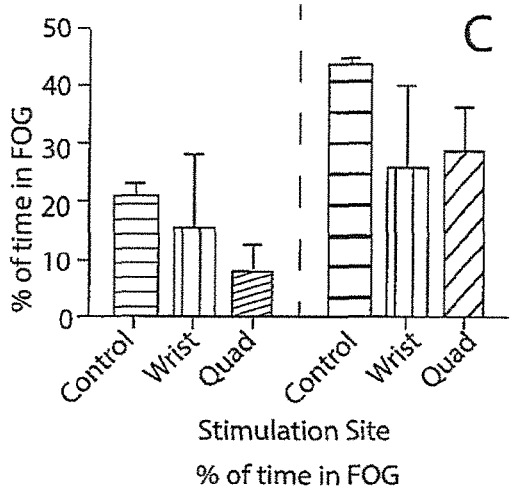

In real life testing, continuous cueing for FOG relief has proved very effective in reducing the time to complete a walking task, increasing walking speed and reducing the percentage of time spent in FOG. FIG. 9 (A) shows the effect of continuous cueing on the amount of time taken to complete a 14 meter walking task when cueing was applied at one of two sites when FOG was detected. FIG. 9 (B) shows the effect of continuous cueing on average walking speed over a 14 meter walking task when cueing was applied at one of two sites when FOG was detected. FIG. 9 (C) plots the effect of continuous cueing on the amount of time spent in a FOG state over the duration of a 14 meters walking task when cueing was applied at one of two sites when FOG was detected.

FOG Prevention

FOG prevention can be in one of two modes; Always ON or Adaptive.

In the always-ON embodiment, cueing is applied whenever the user is not seated, standing still or lying. Intention to stand, or walk activates the stimulator and stimulation is applied until the user stops walking as detected by the gait sensor block in the control unit device (FIGS. 11 and 12).

Figure 10:
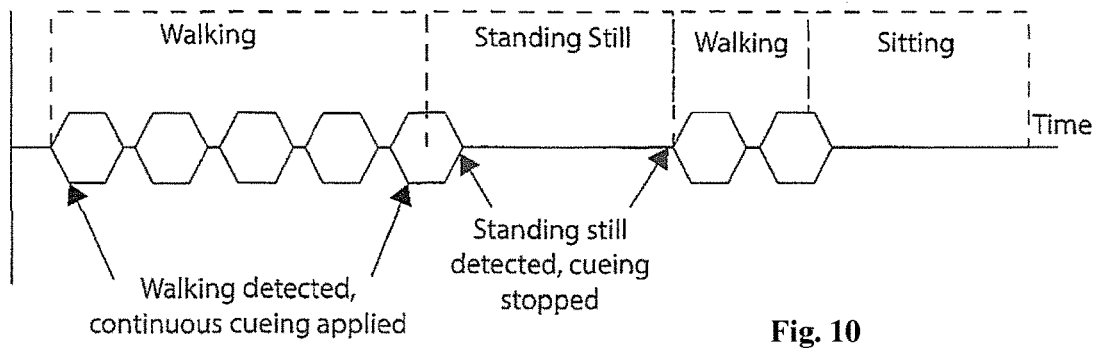
FIG. 10 is a plot illustrating always-on cueing.

FIG. 10 shows always-ON cueing. A continuous cue is applied in response to walking being detected and when the user is not standing or sitting. The frequency of waveform delivery is customizable.

Figure 11:
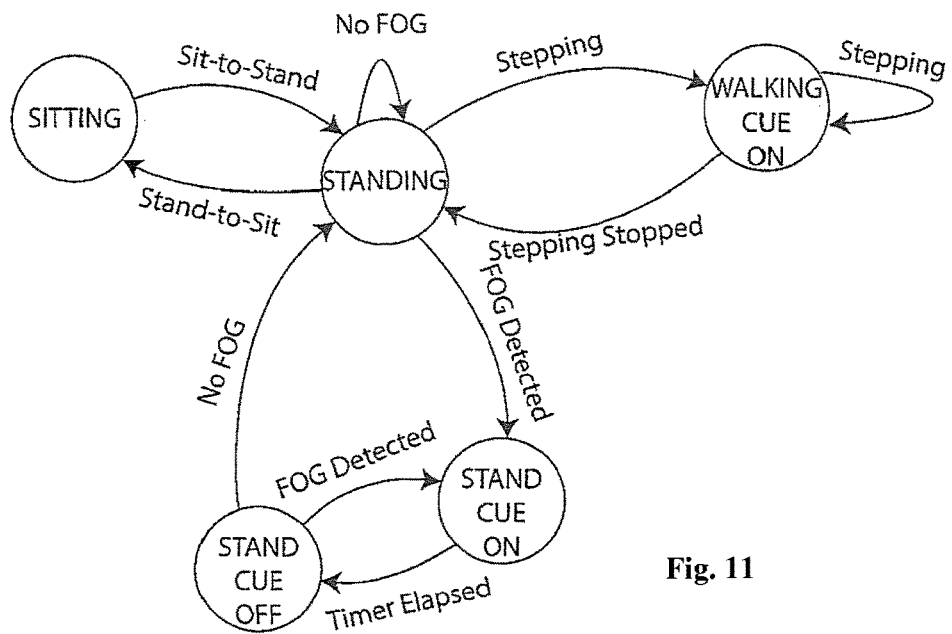
FIG. 11 is a state diagram for always-on operation.
Figure 12:
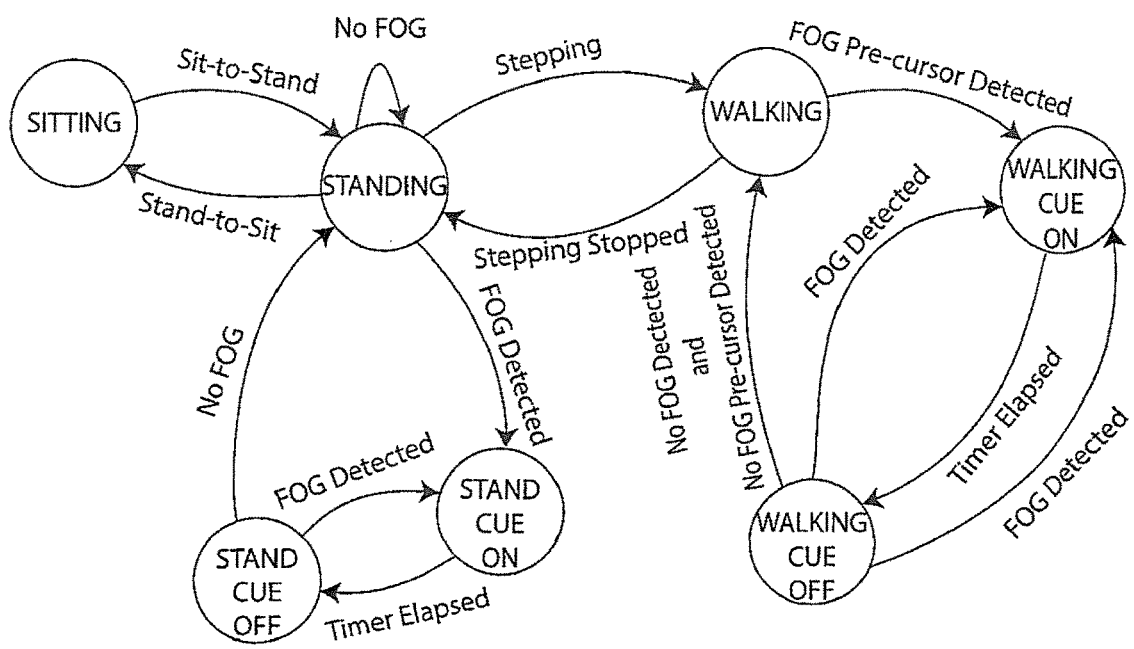
FIG. 12 is such a diagram for adaptive cueing.

FIG. 11 shows a FOG prevention, always-ON cueing state transition diagram. A continuous cue is applied in response to walking being detected and when the user is not standing or sitting. If the user enters a FOG state cueing is delivered in the absence of stepping. The frequency of waveform delivery is customizable.

In another embodiment, cueing (adaptive) involves activation to prevent FOG only in response to alterations in gait dynamics or detection of a FOG pre-cursor, cueing delivery can be Continuous or Burst until the gait correction is achieved. This adaptive type of cueing is an alternative to always-on cueing in cases where the user does not require or wish to have continuous cueing. Signals received from the gait sensors automatically control stimulus delivery (FIG. 12).

FIG. 12 shows a FOG prevention Adaptive cueing state transition diagram. A cue (Continuous or Burst) is applied only when the user is walking when a FOG pre-cursor is detected. If the user enters a FOG state cueing is delivered. The frequency of waveform delivery is customizable.

Additional Embodiments Depending on Peripherals

The apparatus uses electrodes placed either on the surface of the skin or implanted just below the skin surface and requires no third party devices (FIGS. 13, 14, 15, and 16). The invention could be effective using third party gait or tremor sensors to detect gait disturbances. A disturbance in gait can be transmitted to the control unit wirelessly and appropriate stimulation delivered. Additionally third party physiological sensors for heart rate and autonomic nervous system and EEG activity can be used to detect impending FOG events and transmit this information to the control unit wirelessly and appropriate stimulation can be delivered.

Additionally, a complete or partially implanted solution could be adopted. In the partially implanted embodiment a stimulator device could be minimally implanted at appropriate sites and the surface control unit worn at the waist (communicating wirelessly with the implant).

Additionally, sensors could also be implanted and again the sensors are communicating with the surface control unit on the gait status of the patient, which triggers activation of implanted stimulator devices. Additionally, a fully implanted approach could be used where stimulator, controller and sensors could be implanted. The sensors could be used to detect both EMG and provide inertial sensing, giving information on muscle activation and movement, providing a basis for sensing movement, intention to change posture, normal gait and gait disturbance.

Figure 13:
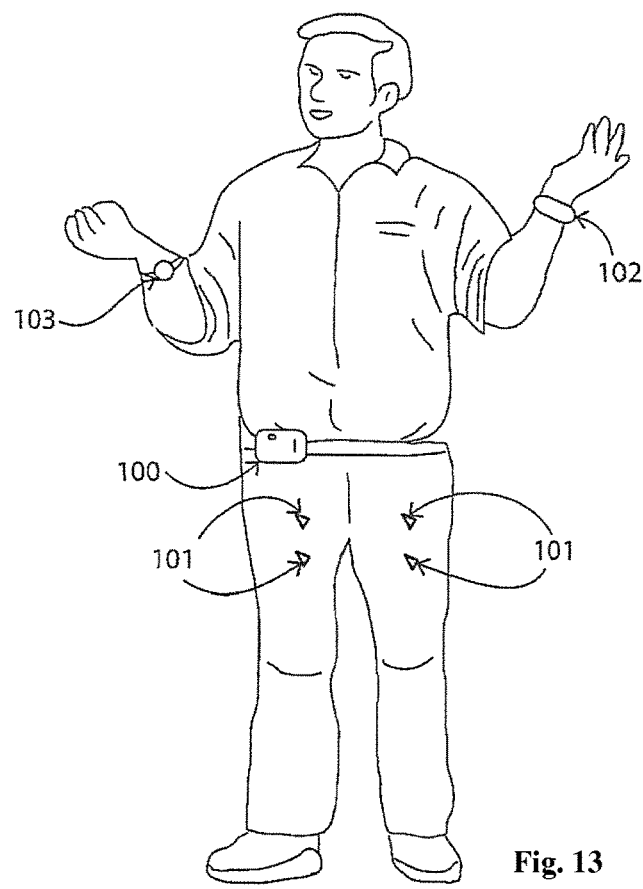
FIG. 13 illustrates wearing of components of an alternative system of the invention.

FIG. 13 shows a control unit 100 being worn attached to a belt or can be placed in a custom belt for easy placement at the waist. There are implanted stimulator devices 101, gait sensors 102, and physiological sensors 103.

Figure 14:
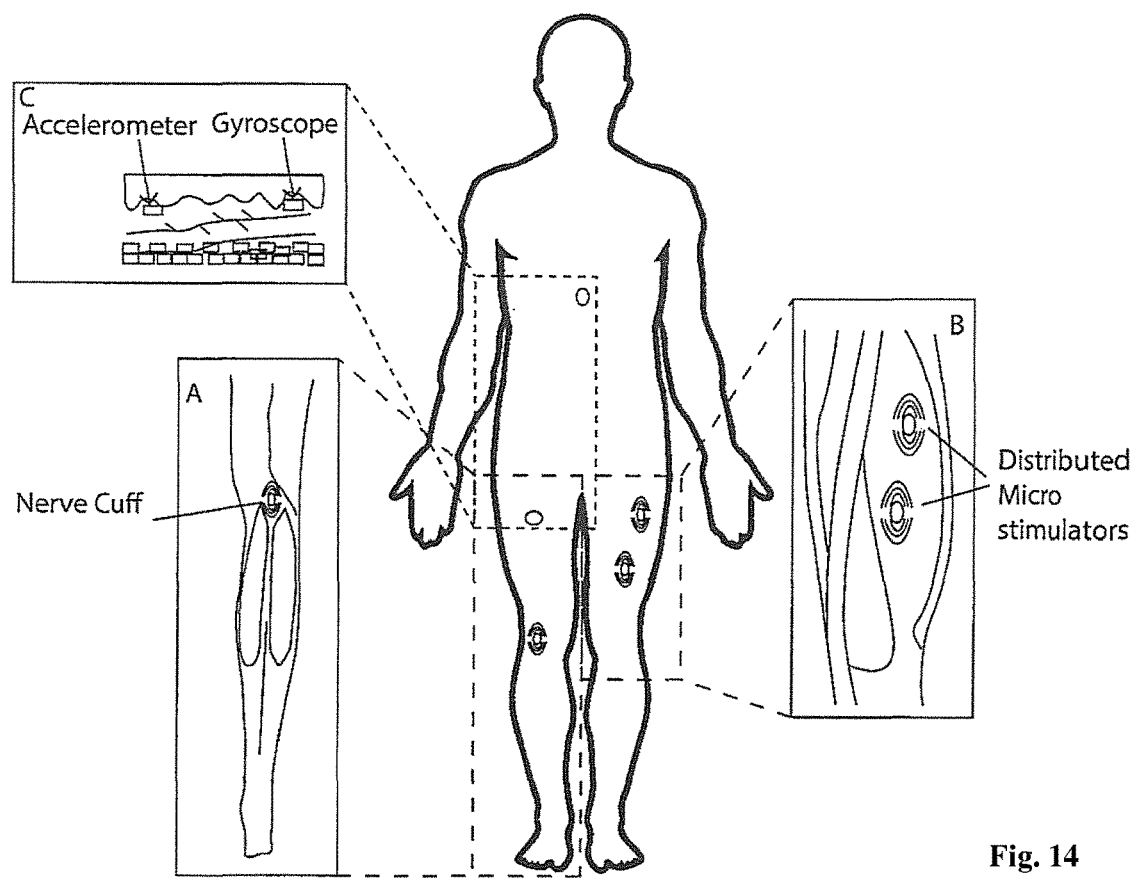
FIG. 14 shows electrical stimulation sites for implanted electrical stimulation cueing.

FIG. 14 is an example of an implanted sensing and cueing arrangement, in which (A) shows use of a nerve cuff electrode for sensory or motor activation, and (B) shows distributed micro-stimulation for sensory or motor activation, and (C) shows implanted distributed sensing for motion sensing.

Figure 15:
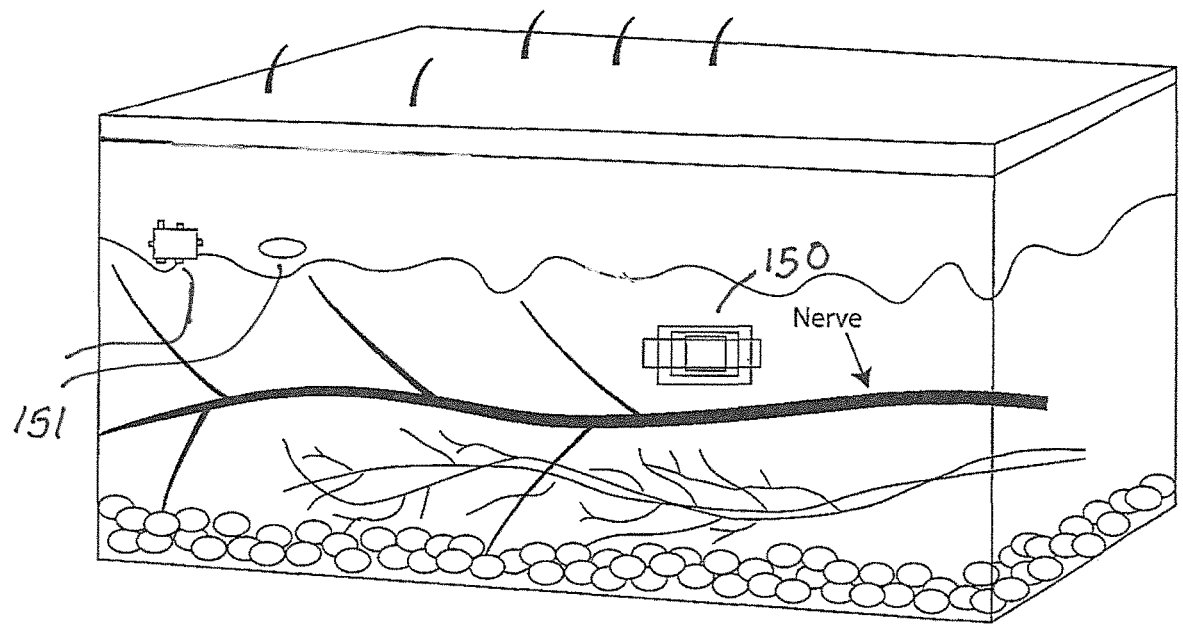
FIG. 15 shows a representation of implanted distributed micro-stimulators and micro-sensor (for motion sense capture) in a cross section of skin, in which the location could be from any appropriate anatomical site on the body suitable for implantation.

FIG. 15 shows an example of the relative position of a distributed micro-stimulation device 150 in the skin compared to underlying nervous tissue. Also shown is an implanted motion sensing unit 151 for motion sense capture (accelerometer or gyroscope). The implantation site for the stimulator device could be any site on the body appropriate for implantation. The implantation site for the motion sense device would be any site on the body appropriate for implantation and gait/posture detection.

Figure 16:
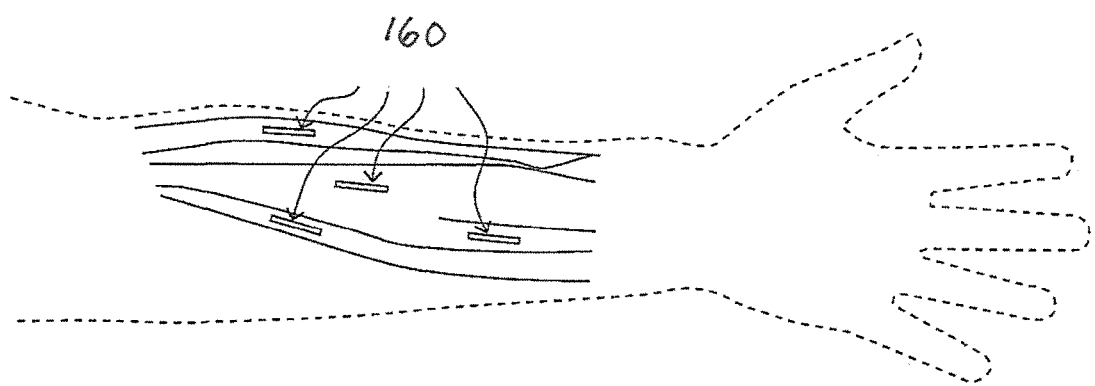
FIG. 16 is a representation of distributed electrical stimulation sites in the forearm, but the location could alternatively be from any appropriate anatomical site on the body suitable for implantation.

FIG. 16 is an example of distributed micro-stimulation setup for sensory or motor activation in the forearm using a BION type stimulation device 160, this arrangement could be employed at any appropriate anatomical site.

Examples of Manual Activation

The cueing system can be activated automatically using the motion sensing block in the control unit or external gait sensors as described previously. Manual activation of the cueing is based on the generation of an interrupt by the motion sensing block in response to a double tap on the control unit enclosure by the patient or using the wrist worn companion device (FIG. 17).

For FOG relief the system is only active when a FOG event occurs. Electrical stimulation can be initiated in one of three ways.
1. By the user tapping directly on the control unit enclosure. This embodiment would deliver burst mode stimulus only.
2. By the user activating a wrist-worn companion device/switch, which is connected to the control unit wirelessly.

In this embodiment pressing or tapping the companion device/switch in a customizable fashion can initiate activation. Additionally activation can be initiated based on an algorithm in the companion device detecting specific actions (motion sense) of the wrist, by user preference the stimulation mode can be continuous or burst in nature.

Figure 17:
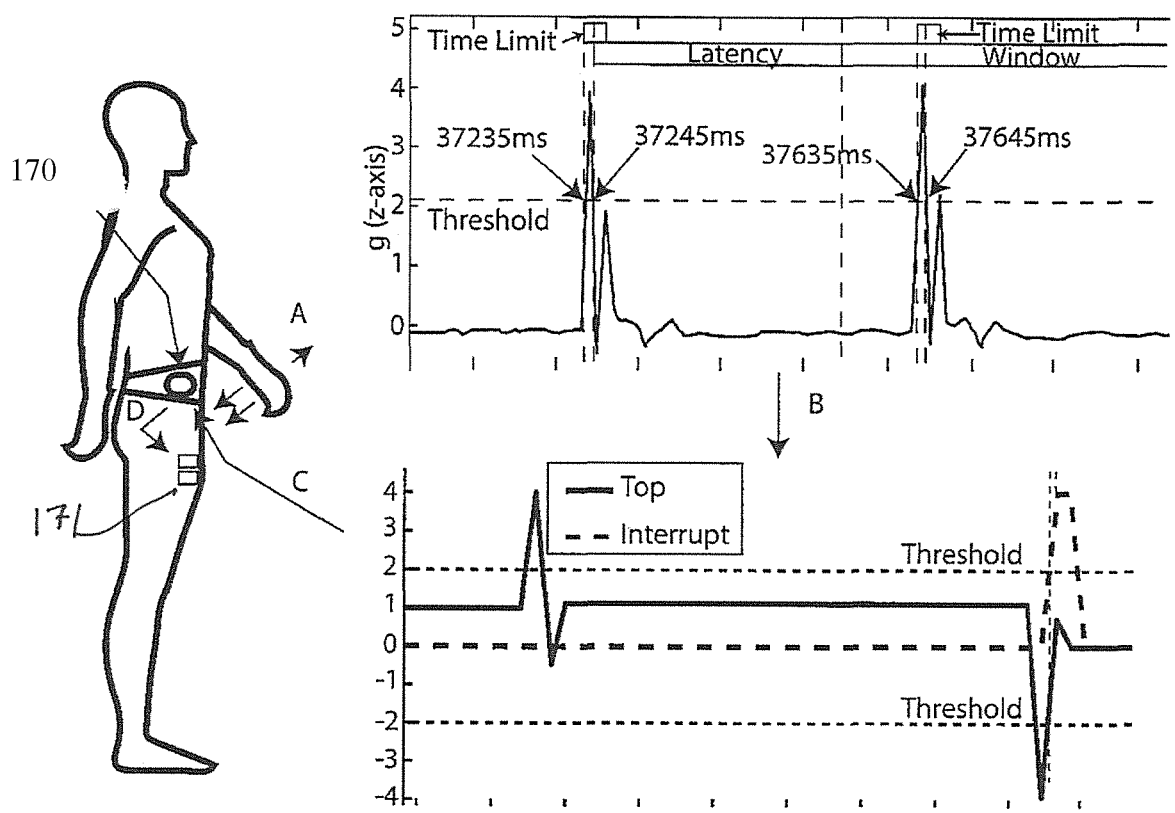
FIG. 17 is a diagram with plots for (A) user enters FOG state and performs a double-tap on the control unit, which is identified by the motion sensor block in the control unit; (B) an interrupt is generated in response to an identifying double tap, and (C) an interrupt is sent to the control unit electrical output stage block to deliver stimulus, and (D) Stimulus is delivered at the electrode site.

FIG. 17 shows manual activation of stimulation by a double-tap on a device enclosure 170. The user enters FOG state and performs a double-tap A on the control unit 170; B, an interrupt is generated in response to identifying a double tap; and C an interrupt is sent to the control unit electrical output stage block to deliver a stimulus; D, Stimulus is delivered at the electrodes 171.

Figure 18:
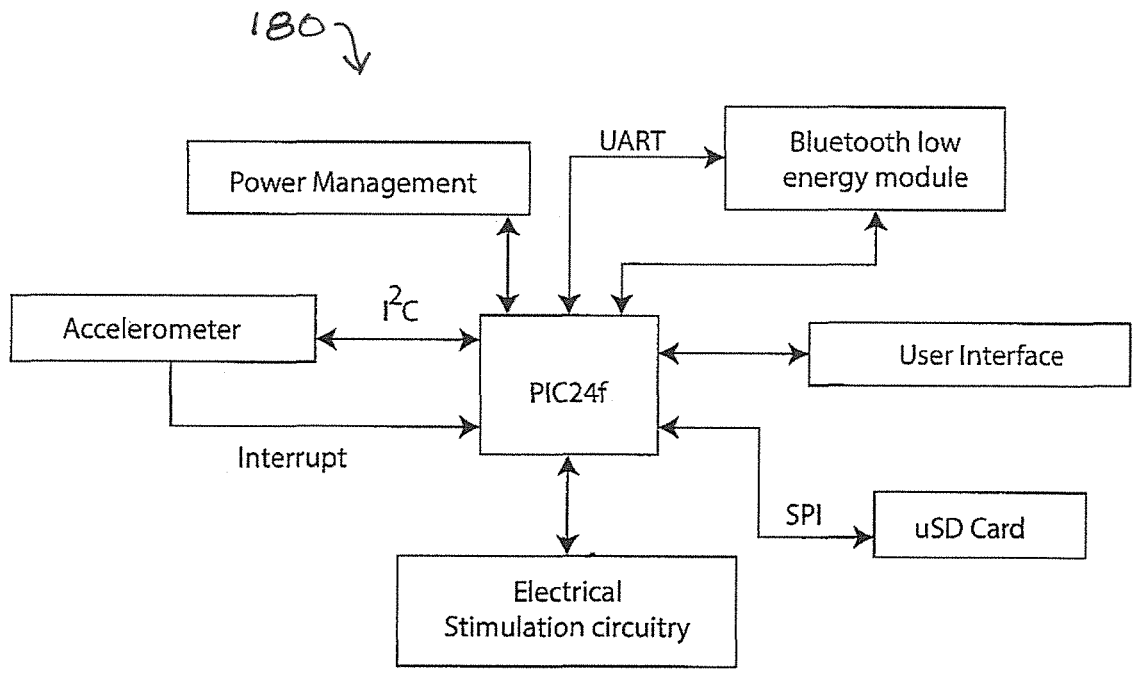
FIG. 18 is a system architecture diagram and FIG. 19 is a more detailed architecture diagram.
Figure 19:
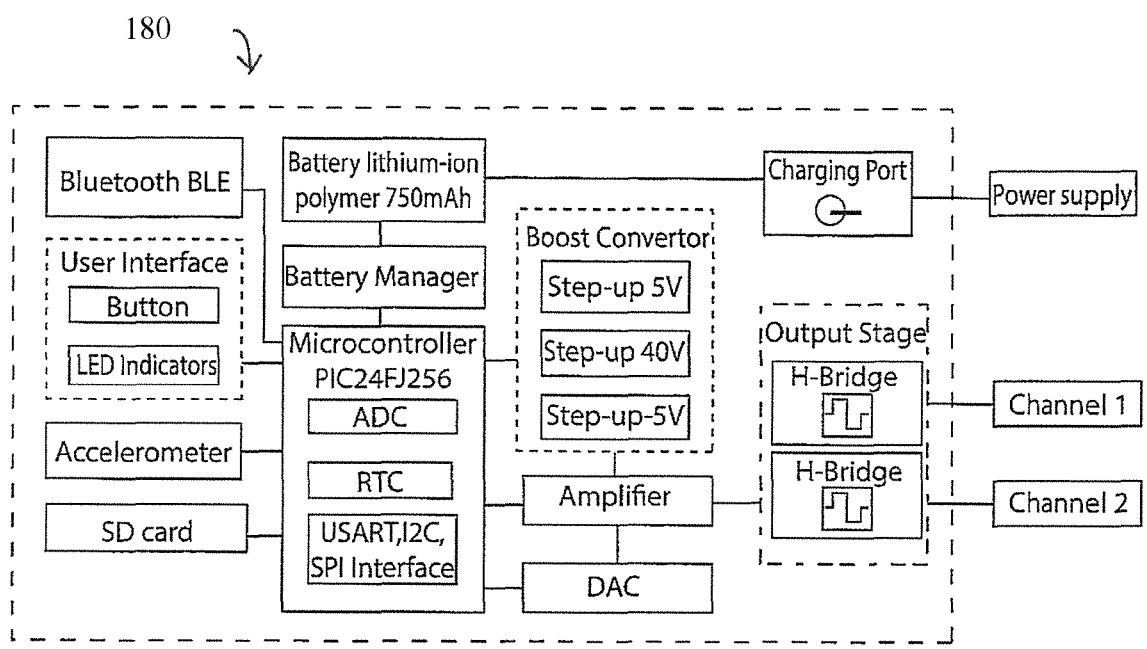

The architecture of a system 180 of one embodiment is shown in FIGS. 18 and 19, in which the controller is a PIC24F processor linked with a power management circuit, an accelerometer motion sensor, electrical stimulation circuitry, a µSD card, a user interface, and a Bluetooth module.

Stimulus Amplitude

The stimulus when delivered by the system is above the user's sensory threshold but below their motor threshold. Thus, the user feels the sensation on their skin but muscle contraction is completely under voluntary control. However, in another embodiment the amplitude of the electrical stimulus could be set sufficiently high so as to achieve a muscle contraction. Thus, the system can deliver sensory cueing and motor cueing. Motor cueing can be employed in a number of scenarios including for step initiation, more aggressive cueing for FOG relief and guidance around objects in the walking pathway. Motor cueing is controlled and activated in a similar manner to sensory cueing.

Example Uses

Table 1 below shows the surface electrical stimulation parameter values which were demonstrated to be highly effective in FOG relief (25% reduction in time to complete a walking task) and FOG prevention (43% reduction in time to complete a walking task) when used during testing on patients with Parkinson's disease using skin surface electrodes on the skin surface of the hamstrings muscle as the site for the electrode pair and when cutaneous multi-modal somatosensory stimulation was applied. The apparatus used was that illustrated in FIGS. 1 and 2 with the electrode position being position D in FIG. 4(b).

TABLE 1

| Stimulation Parameters | FOG Relief mode | FOG Prevention mode |
|---|---|---|
| Stimulation Intensity Voltage | 10-25 V | 10-25 V |
| Pulse Frequency | 36 Hz | 36 Hz |
| Pulse Width | 350 µs | 350 µs |
| Inter-Pulse Interval | 100 µs | 100 µs |
| Ramp-Up Time | 100 ms | 100 ms |
| ON Time | 1000 ms | 500 ms |
| Ramp-Down Time | 100 ms | 100 ms |
| OFF Time | 200 ms | 0 ms (gait cycle time 0.7 s) |

Table 2 below provides representative raw data on the performance of the FOG Relief and FOG Prevention ES versus No ES for two patients with Parkinson's disease. Two outcome measures were used: the number of FOG events occurring during a specified walking task and the time to complete this walking task. It is clear that FOG Relief and FOG Prevention both provide very significant improvements in these outcome measures when the stimulation parameters of Table 1 were applied.

TABLE 2

| Gait Parameters | No ES Patient 1 | FOG Relief Patient 1 | FOG Prevention Patient 1 | No ES Patient 2 | FOG Relief Patient 2 | FOG Prevention Patient 2 |
|---|---|---|---|---|---|---|
| No of FOG Events | 6 | 3 | 0 | 13 | 8 | 6 |
| Time to Complete Walking Task | 82.45 s | 73.13 s | 59.10 s | 139.6 | 109.9 | 85.36 s |

For the performance data in Table 2, FOG Relief ES was initiated by the patient self-activating the delivery of stimulus by performing a double-tap action on the surface of the device enclosure with their hand as illustrated in FIG. 17. This double tap action is detected by an on-board accelerometer (ST Microelectronics LIS2DH™ device was used) and an interrupt was generated by the accelerometer device, provided the double tap 'characteristics' matched the programmed settings in the accelerometer. This interrupt was used to trigger deliver of stimulus.

Table 3 below lists the programmed accelerometer double tap parameters successfully used for the FOG Relief results shown in Table 2 and which are illustrated in FIG. 17. There are four LIS2DH accelerometer double tap parameters, which must be customised to the unique needs of persons with Parkinson's disease due to the speed at which they are typically capable of executing a double tap (typically slower than persons without PD) and due to the force at which they are capable of performing a double tap (typically lower forces than persons without PD).

The first double tap parameter is the Latency (FIG. 17), which is the minimum time which must elapse between the first and the second tap being performed. The second double tap parameter is the Threshold, which is the minimum acceleration which must be detected before the acceleration spike is recognised as a tap. The values given use the unit "g", in which 1 g=9.81 m/s$^2$, the force of the tap being detected as an acceleration on the accelerometer. In general the preferred range is 5 m/s$^2$ to 100 m/s$^2$. The third double tap parameter is the Time Limit, which is the maximum time which can elapse from the acceleration signal exceeding the Threshold to returning below the Threshold. The fourth double tap parameter is the Window, which is the time after the Latency, by which time the second tap must have crossed the Threshold.

The values for these parameters that will be effective with persons with Parkinson's disease have to be determined through experimental means by testing with this patient group. We have carried out this testing.

TABLE 3

| Double Tap Parameters | Accelerometer Double Tap Parameter Range | Value Used in FOG Relief Testing (Table 2 data) |
|---|---|---|
| Latency | 0-635 ms | 175-185 ms |
| Threshold | 2-8 g | 3 g |
| Time Limit | 0-1270 ms | 25 ms |
| Window | 0-1270 ms | 340 ms |

Stimulus Modulation Strategy for Both FOG Prevention and FOG Relief

As described above the controller can dynamically change its mode of operation according to conditions. Examples are "always on", "adaptive", "continuous" and "burst". In various embodiments the controller is programmed to modulate stimuli in real-time using a close loop technique and three dimensional stimulus spaces, an example for cutaneous multi-modal somatosensory electrical stimulation is shown in FIG. 24 and an example for motor multi-modal somatosensory electrical stimulation is shown in FIG. 25.

The controller functions as follows: The stimulus effect can be considered to be the effect of three independent stimulation parameters working together to increase or decrease the effect of the electrical stimulus: Stimulus Intensity Voltage, Ramp Up Time, Pulse Frequency. Two points in stimulus parameters 3D space are identified: the lowest stimulus values considered to work for multi-modal somatosensory electrical stimulation (Stimulus Intensity Voltage 10V, Ramp Up Time 0.4 s, Pulse Frequency 40 Hz) and the highest stimulus values that will maintain the stimulus as non-motor and still function as multi-modal somatosensory electrical stimulation (Stimulus Intensity Voltage 30V, Ramp Up Time 0.0 s, Pulse Frequency 20 Hz). These two points in 3D stimulus space are two diagonally opposite points in a cube as shown in FIG. 24.

The controller is programmed to modulate stimulus intensity by moving along a stimulation modulation profile line from the point of lowest intensity to the point of highest intensity. By using this line, which combines the adjustment of three parameters simultaneously, a more effective and efficient modulation of stimulus is achieved. By way of example, stimulus could be modulated using a 10 s window but the window size could be adjusted to other values to optimize the performance of the controller.

Advantageously, the line may follow any suitable curve according to combinations of the parameters contributing to it. Such relative combinations will vary from patient to patient, and the shape of the line may be pre-set as part of the patient characteristics.

The stimulation modulation profile line is divided into 100 steps from the minimum stimulus point to maximum stimulus point (a larger step number could be adopted, this number being presented by way of example).

FOG Prevention

With the 10 s window, the controller measures the percentage of time the patient was in FOG for the previous 10 s and modulates the stimulus to be used for the next cycle on the basis of this measurement using the flow-chart of FIG. 26.

The patient is detected to be walking, cueing is turned on in the FOG Prevention mode at the lowest stimulus point on the stimulation modulation profile line.

If during the previous 10 s cycle, the FOG incidence was less than or equal 12.5%, then the stimulus parameter point on the stimulation modulation profile line is unchanged.

If during the previous 10 s cycle, the FOG incidence was greater than 12.5% and less than or equal 25%, then the stimulus parameter point on the stimulation modulation profile line is incremented by 5 points.

If during the previous 10 s cycle, the FOG incidence was greater than 25% and less than or equal 50%, then the stimulus parameter point on the stimulation modulation profile line is incremented by 10 points.

If during the previous 10 s cycle, the FOG incidence was greater than 50%, then the stimulus parameter point on the stimulation modulation profile line is incremented by 20 points.

This process is continuously repeated each 10 s cycle with the stimulus point moving along the stimulation modulation profile line as required based on the effectiveness (as measured by the percentage of time in FOG) of the stimulus preventing FOG during the previous cycle.

The rationale for this modulation strategy is that: at low levels of FOG (12.5%<FOG<=25%) the controller adopts a conservative approach in trying to eliminate the low levels of FOG through the gradual increase in stimulus effect, the small increment step here of 5 points gives scope to use twenty 5 increments steps along the stimulation modulation profile line in our efforts to eliminate FOG. At medium levels of FOG (25%<FOG<=25%) there is a less conservative approach in trying to eliminate this medium level of FOG through a larger more aggressive increase in stimulus effect to counter the more frequent FOG. The increment step here of 10 points gives scope to use ten 10 increments steps along the stimulation modulation profile line to eliminate FOG. At high levels of FOG (25%<FOG<=25%) there is a very aggressive approach in trying to eliminate this high level of FOG through a much larger aggressive increase in stimulus effect to counter the more frequent FOG. The increment step here of 20 points gives scope to use five 20 increments steps along the stimulation modulation profile line to eliminate FOG.

In all cases, stimulus intensity is modulated by moving along the stimulation modulation profile line from the point of lowest intensity to the point of highest intensity. By using this line, which combines the adjustment of three parameters simultaneously, a more effective and efficient modulation of stimulus is achieved.

FOG Relief

Prior to using the device, the patient first selects if stimulus will be incremented along the stimulation modulation profile line by 5, 10 or 20 increments with each repeated application of stimulus if FOG persists.

The patient is walking and FOG is detected and a burst of cueing is activated at the lowest stimulus point on the stimulation modulation profile line.

If after 5 s (other time periods could also be used), FOG still exists, then the stimulus parameter point on the stimulation modulation profile line is incremented by the preselected step point (5, 10 or 20 steps) and another burst of stimulus is applied.

This process is continued until either FOG ends or the end point of the stimulation modulation profile line is reached.

The rationale for this modulation strategy is that the patient decides on how aggressively stimulus will be increased to relieve FOG if it persists. Stimulus intensity is modulated by moving along the stimulation modulation profile line from the point of lowest intensity to the point of highest intensity. By using this line, which combines the adjustment of three parameters simultaneously, a more effective and efficient modulation of stimulus is achieved.

It will be appreciated that the invention is capable of operating effectively in environments with rapidly varying noise levels and in environments with rapidly varying light levels.

For PD patients FOG is a sudden, involuntary, and transient block in gait, typically occurring at gait initiation, turning, approaching targets, and passing narrow doorways and manifests as moving forward with very small steps, leg trembling in place, or total akinesia. The quality of life of patients is seriously affected by FOG, because it results in an unpredictable loss of control over movement and often results in falls, which are a major cause of hospitalization for PD patients. Our invention makes FOG relief and prevention feasible, unobtrusive with minimum burden on the patient and has wide application in almost any environment both inside and outside the home.

The invention is not limited to the embodiments described but may be varied in construction and detail.

The invention claimed is:

1. A gait management apparatus comprising:
   at least one motion sensor configured for sensing motion of a user,
   at least one cueing actuator including electrical stimulation electrodes, the electrical stimulation electrodes configured for stimulating a body part of the user,
   a memory for storing a non-transitory computer program, and
   a controller programmed to execute the program stored in the memory to allow the controller to receive motion sensing signals from said at least one motion sensor, to perform automatic detection of a gait dysfunction or potential gait dysfunction, and to activate said cueing actuator automatically upon said detection, wherein the at least one motion sensor, the at least one cueing actuator, the electrical stimulation electrodes, the memory, and the controller are in electrical contact,
   wherein the controller and the cueing actuator are programmed to perform at least one selected from the group consisting of sensory level cueing and motor level cueing,
   and
   wherein the controller is programmed to determine characteristics of a patient and to activate cueing customised to the patient.

2. The gait management apparatus as claimed in claim 1, wherein said gait dysfunction is freezing of gait.

3. The gait management apparatus as claimed in claim 1, wherein said characteristics include skin impendence, and/or sensory threshold, and/or motor threshold, and/or pain threshold, and/or pain tolerance.

4. The gait management apparatus as claimed in claim 1, wherein said characteristics include the patient's changing response to motor level stimulation as a cue and/or the patient's changing response to sensory level stimulation as a cue.

5. The gait management apparatus as claimed in claim 1, wherein the controller is programmed to activate the cueing actuator to prevent gait dysfunction when the controller senses that a patient is walking or has an intention to walk.

6. The gait management apparatus as claimed in claim 1, wherein the controller is programmed to apply electrical stimulation cueing at an intensity level which is insufficient for functional muscle contraction, in which said cueing includes stimulation of either afferent or efferent nerves, in which afferent nerve stimulation causes a patient central nervous system to cause an action, and efferent nerve stimulation directly causes a muscle contraction with consequent triggering of afferent nerves causing the patient's central nervous system to trigger an action giving rise to a natural motor response, and in which said efferent nerve cueing is at an intensity level which is insufficient for functional muscle contraction.

7. The gait management apparatus as claimed in claim 1, wherein the controller is programmed to apply electrical stimulation cueing at an intensity level which is insufficient for functional muscle contraction, in which said cueing includes stimulation of either afferent or efferent nerves, in which afferent nerve stimulation causes a patient central nervous system to cause an action, and efferent nerve stimulation directly causes a muscle contraction with consequent triggering of afferent nerves causing the patient's central nervous system to trigger an action giving rise to a natural motor response, and in which said efferent nerve cueing is at an intensity level which is insufficient for functional muscle contraction; and wherein the controller is programmed to control cueing to exceed a multi-modal somatosensory threshold but not to cause a functional muscular contraction, in which electrode stimulation intensity is across a full continuum from a simple muscle twitch response up to but not including a muscle contraction of sufficient intensity as would aid in the execution of a functional movement.

8. The gait management apparatus as claimed in claim 1, wherein the controller is programmed to activate the cueing actuator to prevent gait dysfunction when the controller senses that a patient is walking or has an intention to walk; and wherein the controller is programmed to operate in a continuous cueing mode or an adaptive cueing mode, in which:
  in the continuous mode, cueing is performed whenever the user is not seated, standing still or lying, in which cueing is performed upon detection of intention to walk until the controller determines that the user stops walking, and
  in the adaptive mode cueing is performed to prevent freezing-of-gait only in response to alterations in gait dynamics or detection of a freezing-of-gait pre-cursor.

9. The gait management apparatus as claimed in claim 1, wherein the controller is programmed to activate cueing with a series of bursts until it automatically determines that gait dysfunction has ended.

10. The gait management apparatus as claimed in claim 1, wherein the controller is programmed to dynamically modify cueing in real time according to conditions.

11. The gait management apparatus as claimed in claim 1, wherein the controller is programmed to dynamically modify cueing in real time according to conditions; and wherein the controller is programmed to modulate stimuli in real-time using closed loop control.

12. The gait management apparatus as claimed in claim 1, wherein the controller is programmed to dynamically modify cueing in real time according to conditions; and wherein the controller is programmed to modulate stimuli in real-time using closed loop control; and wherein the controller is programmed to maintain and monitor at least one three dimensional stimulus space, one for cutaneous multi-modal somatosensory electrical stimulation and/or one for motor multi-modal somatosensory electrical stimulation.

13. The gait management apparatus as claimed in claim 1, wherein the controller is programmed to dynamically modify cueing in real time according to conditions; and wherein the controller is programmed to modulate stimuli in real-time using closed loop control; and wherein the controller is programmed to maintain and monitor at least one three dimensional stimulus space, one for cutaneous multi-modal somatosensory electrical stimulation and/or one for motor multi-modal somatosensory electrical stimulation; and wherein the controller is programmed to manage a stimulus effect of independent stimulation parameters working together to increase or decrease the effect of the electrical stimulus.

14. The gait management apparatus as claimed in claim 1, wherein the controller is programmed to dynamically modify cueing in real time according to conditions; and wherein the controller is programmed to modulate stimuli in real-time using closed loop control; and wherein the controller is programmed to maintain and monitor at least one three dimensional stimulus space, one for cutaneous multi-modal somatosensory electrical stimulation and/or one for motor multi-modal somatosensory electrical stimulation; and wherein the controller is programmed to manage a stimulus effect of independent stimulation parameters working together to increase or decrease the effect of the electrical stimulus; and wherein said parameters include stimulus intensity voltage, ramp-up time, and pulse Frequency.

15. The gait management apparatus as claimed in claim 1, wherein the controller is programmed to dynamically modify cueing in real time according to conditions; and wherein the controller is programmed to modulate stimuli in real-time using closed loop control; and wherein the controller is programmed to maintain and monitor at least one three dimensional stimulus space, one for cutaneous multi-modal somatosensory electrical stimulation and/or one for motor multi-modal somatosensory electrical stimulation; and wherein the controller is programmed to manage a stimulus effect of independent stimulation parameters working together to increase or decrease the effect of the electrical stimulus; and wherein the controller is programmed to identify stimulus effect points in multi-dimensional space including lowest stimulus values considered to work for multi-modal somatosensory electrical stimulation and highest stimulus values that will maintain the stimulus as non-motor and still function as multi-modal somatosensory electrical stimulation.

16. The gait management apparatus as claimed in claim 1, wherein the controller is programmed to dynamically modify cueing in real time according to conditions; and wherein the controller is programmed to modulate stimuli in real-time using closed loop control; and wherein the controller is programmed to maintain and monitor at least one three dimensional stimulus space, one for cutaneous multi-modal somatosensory electrical stimulation and/or one for motor multi-modal somatosensory electrical stimulation; and wherein the controller is programmed to manage a stimulus effect of independent stimulation parameters working together to increase or decrease the effect of the electrical stimulus; and wherein the controller is programmed to identify stimulus effect points in multi-dimensional space including lowest stimulus values considered to work for multi-modal somatosensory electrical stimulation and highest stimulus values that will maintain the stimulus as non-motor and still function as multi-modal somatosensory electrical stimulation; and wherein the controller is programmed to modulate stimulus intensity by moving along a stimulation modulation profile line from a point of lowest intensity to a point of highest intensity with adjustment of all parameters simultaneously, using an adjustable window size.

17. The gait management apparatus as claimed in claim 1, wherein the controller is programmed to dynamically modify cueing in real time according to conditions; and wherein the controller is programmed to modulate stimuli in real-time using closed loop control; and wherein the controller is programmed to maintain and monitor at least one three dimensional stimulus space, one for cutaneous multi-modal somatosensory electrical stimulation and/or one for motor multi-modal somatosensory electrical stimulation; and wherein the controller is programmed to manage a stimulus effect of independent stimulation parameters working together to increase or decrease the effect of the electrical stimulus; and wherein the controller is programmed to identify stimulus effect points in multi-dimensional space including lowest stimulus values considered to work for multi-modal somatosensory electrical stimulation and highest stimulus values that will maintain the stimulus as non-motor and still function as multi-modal somatosensory electrical stimulation; and wherein the controller is programmed to modulate stimulus intensity by moving along a stimulation modulation profile line from a point of lowest intensity to a point of highest intensity with adjustment of all parameters simultaneously, using an adjustable window size; and wherein the controller is programmed to divide the stimulation modulation profile line into multiple steps from a minimum stimulus point to a maximum stimulus point.

18. The gait management apparatus as claimed in claim 1, wherein the controller is programmed to dynamically modify cueing in real time according to conditions; and wherein the controller is programmed to operate in a freezing-of-gait prevention mode in which the controller measures a percentage of time the patient was in a freezing-of-gait state for a last time window and modulates stimulus to be used for a next cycle on the basis of this measurement.

19. The gait management apparatus as claimed in claim 1, wherein the controller is programmed to dynamically modify cueing in real time according to conditions; and wherein the controller is programmed to operate in a freezing-of-gait prevention mode in which the controller measures a percentage of time the patient was in a freezing-of-gait state for a last time window and modulates stimulus to be used for a next cycle on the basis of this measurement; and wherein the controller is programmed to operate in the freezing-of-gait prevention mode at a lowest stimulation point while the patient is detected to be walking.

20. The gait management apparatus as claimed in claim 1, wherein the controller is programmed to dynamically modify cueing in real time according to conditions; and wherein the controller is programmed to modulate stimuli in real-time using closed loop control; and wherein the controller is programmed to maintain and monitor at least one three dimensional stimulus space, one for cutaneous multi-modal somatosensory electrical stimulation and/or one for motor multi-modal somatosensory electrical stimulation; and wherein the controller is programmed to manage a stimulus effect of independent stimulation parameters working together to increase or decrease the effect of the electrical stimulus; and wherein the controller is programmed to identify stimulus effect points in multi-dimensional space including lowest stimulus values considered to work for multi-modal somatosensory electrical stimulation and highest stimulus values that will maintain the stimulus as non-motor and still function as multi-modal somatosensory electrical stimulation; and wherein the controller is programmed to modulate stimulus intensity by moving along a stimulation modulation profile line from a point of lowest intensity to a point of highest intensity with adjustment of all parameters simultaneously, using an adjustable window size; and wherein the controller is programmed to divide the stimulation modulation profile line into multiple steps from a minimum stimulus point to a maximum stimulus point; and wherein the controller is programmed to move along the line according to the extent of freezing-of-gait detected in a previous time window.

21. The gait management apparatus as claimed in claim 1, wherein the controller is programmed to dynamically modify cueing in real time according to conditions; and wherein the controller is programmed to modulate stimuli in real-time using closed loop control; and wherein the controller is programmed to maintain and monitor at least one three dimensional stimulus space, one for cutaneous multi-modal somatosensory electrical stimulation and/or one for motor multi-modal somatosensory electrical stimulation; and wherein the controller is programmed to manage a stimulus effect of independent stimulation parameters working together to increase or decrease the effect of the electrical stimulus; and wherein the controller is programmed to identify stimulus effect points in multi-dimensional space including lowest stimulus values considered to work for multi-modal somatosensory electrical stimulation and highest stimulus values that will maintain the stimulus as non-motor and still function as multi-modal somatosensory electrical stimulation; and wherein the controller is programmed to modulate stimulus intensity by moving along a stimulation modulation profile line from a point of lowest intensity to a point of highest intensity with adjustment of all parameters simultaneously, using an adjustable window size; and wherein the controller is programmed to choose per-patient a line to follow as part of the patient characteristics.

22. The gait management apparatus as claimed in claim 1, wherein the controller is configured to dynamically modify cueing in real time according to conditions; and wherein the controller is programmed to operate in a freezing-of-gait relief mode in which there is progressively greater stimuli applied in steps along said profile line until freezing-of-gait has stopped.

23. The gait management apparatus as claimed in claim 1, wherein the controller is programmed to dynamically modify cueing in real time according to conditions; and wherein the controller is programmed to operate in a freezing-of-gait relief mode in which there is progressively greater stimuli applied in steps along said profile line until freezing-of-gait has stopped; and wherein the controller is programmed to receive a user input of how aggressively stimulus will be increased to relieve freezing-of-gait if it persists.

24. The gait management apparatus as claimed in claim 1, wherein at least one actuator pair of electrodes is arranged to be skin surface mounted.

25. The gait management apparatus as claimed in claim 1, wherein at least one actuator pair of electrodes is arranged to be implanted under a patient's skin.

26. The gait management apparatus as claimed in claim 1, further comprising a patient interface, and wherein the controller is programmed to activate cueing in response to a manual cueing instruction at said interface.

27. The gait management apparatus as claimed in claim 1, further comprising a patient interface, and wherein the controller is programmed to activate cueing in response to a manual cueing instruction at said interface; and wherein the interface comprises a button for manual cueing activation.

28. The gait management apparatus as claimed in claim 1, further comprising a patient interface, and wherein the controller is programmed to activate cueing in response to a manual cueing instruction at said interface; and wherein the controller is programmed to recognise at least one tap as a patient trigger to activate cueing.

29. The gait management apparatus as claimed in claim 1, further comprising a patient interface, and wherein the controller is programmed to activate cueing in response to a manual cueing instruction at said interface; and wherein the controller is programmed to be customised to parameters specific to a patient for recognising taps.

30. The gait management apparatus as claimed in claim 1, wherein the controller is programmed to recognise a series of multiple taps as said patient trigger; and wherein the controller is programmed to recognise said taps if they comply with parameters of (a) latency, being a minimum time which must elapse between the first and the second tap being performed, (b) threshold, which is a minimum acceleration which must be detected before an acceleration spike is recognised as a tap, (c) time limit, which is the maximum time which can elapse from the acceleration signal exceeding the threshold to returning below the threshold, and (d) window, which is the time after the latency, by which time the subsequent tap must have crossed the threshold.

31. The gait management apparatus as claimed in claim 1, wherein the controller is programmed to recognise at least one tap as a patient trigger to activate cueing; and wherein the controller is programmed to recognise said tapping on an enclosure of the controller.

32. The gait management apparatus as claimed in claim 1, wherein the controller is programmed to recognise at least one tap as a patient trigger to activate cueing; and wherein the apparatus comprises at least one accelerometer linked with the controller and the controller is programmed to use inputs from said accelerometer as tap inputs.

33. The gait management apparatus as claimed in claim 1, wherein at least one cueing actuator is wirelessly linked with the controller, and the controller may include a smartphone programmed with apparatus control software.

34. The gait management apparatus as claimed in claim 1, wherein at least one cueing actuator is configured to be worn, for example wrist-worn.

35. The gait management apparatus as claimed in claim 1, wherein the cueing actuator includes a mechanical stimulation device.

36. The gait management apparatus as claimed in claim 1, wherein the cueing actuator includes a mechanical stimulation device; and wherein the mechanical stimulation device is configured to perform mechanical vibration.

37. The gait management method as claimed in claim 1, wherein the controller applies electrical stimulation cueing at an intensity level which is insufficient for functional muscle contraction, in which said cueing includes stimulation of either afferent or efferent nerves, in which afferent nerve stimulation causes a patient central nervous system to cause an action, and efferent nerve stimulation directly causes a muscle contraction with consequent triggering of afferent nerves causing the patient's central nervous system to trigger an action giving rise to a natural motor response, and in which said efferent nerve cueing is at an intensity level which is insufficient for functional muscle contraction; and wherein the controller controls cueing to exceed a multi-modal somatosensory threshold but not to cause a functional muscular contraction, in which electrode stimulation intensity is across a full continuum from a twitch response up to but not including a muscle contraction of sufficient intensity as would aid in the execution of a functional movement.

* * * * *